United States Patent
Greenbaum et al.

(10) Patent No.: US 11,596,618 B2
(45) Date of Patent: Mar. 7, 2023

(54) ORAL CANNABINOID DELIVERY FORMULATIONS WITH MOUTHFEEL EXPERIENCE ENHANCERS

(71) Applicant: Resurgent Biosciences, Inc., Minneapolis, MN (US)

(72) Inventors: Eric Greenbaum, Minneapolis, MN (US); Emily Leuer, Minneapolis, MN (US); Nikolaus Goran, Minneapolis, MN (US); Justin Bueno, Minneapolis, MN (US)

(73) Assignee: Resurgent Biosciences, Inc., Minneapolis, MN (US)

( * ) Notice: Subject to any disclaimer, the term of this patent is extended or adjusted under 35 U.S.C. 154(b) by 0 days.

(21) Appl. No.: 17/150,418

(22) Filed: Jan. 15, 2021

(65) Prior Publication Data

US 2021/0212983 A1    Jul. 15, 2021

Related U.S. Application Data

(60) Provisional application No. 62/961,539, filed on Jan. 15, 2020.

(51) Int. Cl.

| | | |
|---|---|---|
| *A61K 31/352* | (2006.01) | |
| *A61K 31/05* | (2006.01) | |
| *A61K 47/69* | (2017.01) | |
| *A61K 47/54* | (2017.01) | |
| *A61K 45/06* | (2006.01) | |
| *A61K 9/107* | (2006.01) | |
| *A61K 47/36* | (2006.01) | |
| *A61K 47/10* | (2017.01) | |
| *A61K 47/46* | (2006.01) | |
| *A61K 9/00* | (2006.01) | |

(52) U.S. Cl.
CPC .......... *A61K 31/352* (2013.01); *A61K 9/0056* (2013.01); *A61K 9/1075* (2013.01); *A61K 31/05* (2013.01); *A61K 45/06* (2013.01); *A61K 47/10* (2013.01); *A61K 47/36* (2013.01); *A61K 47/46* (2013.01); *A61K 47/549* (2017.08); *A61K 47/6951* (2017.08)

(58) Field of Classification Search
CPC .... A61K 47/10; A61K 9/1075; A61K 31/352; A61K 47/549; A61K 31/05; A61K 45/06; A61K 47/36; A61K 9/0056; A61K 47/46; A61K 47/6951; A61K 9/145; A23L 29/35; A23L 27/00; A23L 27/88; A23L 33/105

See application file for complete search history.

(56) References Cited

U.S. PATENT DOCUMENTS

| | | | | |
|---|---|---|---|---|
| 2003/0215532 A1* | 11/2003 | Nakatsu | ............ | A23G 3/36 514/699 |
| 2013/0216649 A1* | 8/2013 | Anastasiou | ............ | A23G 4/00 426/5 |
| 2013/0274342 A1* | 10/2013 | Ginski | ............ | A61P 11/14 514/662 |
| 2015/0136160 A1* | 5/2015 | Gordon | ............ | A61K 36/46 131/359 |
| 2015/0374770 A1* | 12/2015 | Crowley | ............ | A61K 36/185 424/725 |
| 2016/0051510 A1* | 2/2016 | Allen | ............ | A61K 31/352 424/443 |
| 2016/0220593 A1* | 8/2016 | Anastassov | ............ | A23G 1/40 |
| 2018/0042845 A1* | 2/2018 | Sinai | ............ | A61K 47/10 |
| 2020/0276116 A1* | 9/2020 | Bruun | ............ | A23G 4/10 |

FOREIGN PATENT DOCUMENTS

| | | | | |
|---|---|---|---|---|
| WO | WO-2012125142 A1 * | 9/2012 | ............ | A23L 27/72 |
| WO | WO-2020051055 A2 * | 3/2020 | ............ | A61K 31/352 |

* cited by examiner

*Primary Examiner* — Doan T Phan
(74) *Attorney, Agent, or Firm* — Dicke, Billig & Czaja, PLLC

(57) ABSTRACT

Oral formulations comprising at least one cannabinoid and at least one mouthfeel experience enhancer are described. For example, methods and materials for preparing a dissolvable lozenge comprising a combination of THC and CBD and Szechuan peppercorn or an extract thereof are provided.

4 Claims, No Drawings

ORAL CANNABINOID DELIVERY FORMULATIONS WITH MOUTHFEEL EXPERIENCE ENHANCERS

BACKGROUND OF THE INVENTION

More and more jurisdictions legalize recreational and medical use of *cannabis*. At the same time, *cannabis* use is becoming more widespread, it is also become more scrutinized. Pulmonary delivery, either via smoking or vaporization remains the preferred delivery route for *cannabis* administration due to historical factors and also the favorable pharmacokinetic profile of pulmonary delivery. For example, pulmonary delivery achieves a rapid onset of enhanced well-being and relaxation with an intensification of ordinary sensory experiences. The pulmonary delivery paradigm also offers an experiential aspect to *cannabis* administration which is appealing to many users. One of the issues that has come to light recently is the potentially unpredictable side effects of vaporization, especially in the context of poorly characterized additives. Even assuming that vaporization of *cannabis* and *cannabis* formulations is safe, the vaporization route of administration is uncomfortable, or undesirable for many users. Thus, there is a need for new formulations that combine the pharmacokinetic properties of *cannabis* with improved experiential effects when delivered via the oral cavity.

SUMMARY

The present disclosure describes cannabinoid formulations adapted for oral administration that also provide an enhanced sensory experience in the mouth by incorporation of one or more mouthfeel experience enhancers.

In a first aspect, the present disclosure provides an oral formulation comprising at least one cannabinoid and at least one mouthfeel experience enhancer. The at least one cannabinoid can be selected from the group consisting of THC, THCA, CBD, CBDA, CBG, CBC, THCV, and combinations thereof. The at least one cannabinoid can be complexed with a cyclodextrin, a sugar, or a sugar alcohol. The at least one cannabinoid can be complexed with isomalt. The at least one mouthfeel experience enhancer can selected from the group consisting of a warming agent, tingling agent, cooling agent, puckering agent and sialagogue. The at least one mouthfeel experience enhancer can be a warming agent selected from the group consisting of vanillyl alcohol n-butylether; vanillyl alcohol n-propylether; vanillyl alcohol isopropylether; vanillyl alcohol isobutylether; vanillyl alcohol n-aminoether; vanillyl alcohol isoamylether; vanillyl alcohol n-hexylether; vanillyl alcohol methylether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amylalcohol; benzyl alcohol; glycerine; chloroform; eugenol; cinnamon oil; cinnamic aldehyde; phosphate derivatives thereof; and combinations thereof. The at least one mouthfeel experience enhancer can be a tingling agent selected from the group consisting of Jambu oleoresin, spilanthol; Japanese pepper extract, saanshool-I, saanshool-II, sanshoamide, Sichuan pepper, hydroxy-alpha sanshool; black pepper extract, chavicine, piperine; *Echinacea* extract, Northern Prickly Ash extract, and red pepper oleoresin or a compound that generates effervescence. The at least one mouthfeel experience enhancer can be a cooling agent selected from the group consisting of xylitol, erythritol, dextrose, sorbitol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide, N-ethyl-p-menthane-3-carboxamide, isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol, menthone glycerol ketals, 3-1-menthoxypropane-1,2-diol, menthyl lactate, WS-30, WS-14, *Eucalyptus* extract, p-Menthane-3,8-Diol, Menthol, Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; and Menthol methyl ether, and menthyl pyrrolidone carboxylate. The at least one mouthfeel experience enhancer can be a puckering agent selected from the group consisting of gluconolactone, citric acid, malic acid, acetic acid, phosphoric acid, tartaric acid, lactic acid, fumaric acid, succinic acid adipic acid, ascorbic acid, butyric acid, formic acid, fumaric acid, glyconic acid, phosphoric acid, oxalic acid, succinic acid, and mixtures thereof; or the at least one mouthfeel experience enhancer can be a sialogogue selected from the group consisting of pilocarpine, N,N-disubstituted phenylalkylamines, N,N disubstituted-2-phenylcyclopropylamines; spirooxathiolane-quinnuclidine; *Heliopsis* longpipes root; cholinesterase inhibitors; and mixtures thereof. The oral formulation can further include at least one additional active agent selected from the group consisting of essential oils, herbal extracts, probiotics, homeopathic remedies, flower essences and combinations thereof. The oral formulation can be configured to provide immediate release, a combination of immediate and sustained release, zero order sustained release, time programmed release, bimodal release, or pulsatile release of the at least one cannabinoid or the at least one mouthfeel experience enhancer. The oral formulation can be selected from the group consisting of compressed tablets, rapid orally dissolvable tablets, lozenges, buccal tablets, oral solutions, oral spray, mucoadhesive tablets, and mucoadhesive films. The oral formulation can be a dissolvable lozenge, the at least one cannabinoid can include a combination of THC and CBD in a ratio of between 1:50 and 50:1, the mouthfeel experience enhancer can include Szechuan peppercorn or an extract thereof, wherein the lozenge has a total cannabinoid content between 1 mg and 10 mg. The oral formulation can be a dissolvable lozenge comprising a core and an outer layer, wherein the core comprises a first cannabinoid and the outer layer comprises a first mouthfeel experience enhancer. The dissolvable lozenge can further include an intermediate layer disposed between the core and the outer layer, wherein the core further comprises a second mouthfeel experience enhancer, the intermediate layer comprises a second cannabinoid and a third mouthfeel experience enhancer, and the outer layer further comprises at least a third cannabinoid. The first, the second, and the third mouthfeel experience enhancers can be independently selected from the group consisting of a warming agent, tingling agent, cooling agent, puckering agent and sialagogue. The first, the second and the third cannabinoids cam be independently selected from the group consisting of THC, THCA, CBD, CBDA, CBG, CBC, THCV, and combinations thereof. The formulation cam be an oral solution comprising the at least one cannabinoid in an emulsion, microemulsion, or nanoemulsion. The at least one cannabinoid can be a water-soluble cannabinoid powder comprising at least one cannabinoid oil, at least one sugar or sugar alcohol, at least one hydrocolloid selected from the group consisting of gelatin, gum *acacia*, carob gum, carrageenan, ghatti gum, guar gum, karaya gum, pectin, tragacanth gum, locust bean gum, xanthan gum and combinations thereof, and optionally an emulsifier. The at least one sugar or sugar alcohol can be isomalt, the at least one hydrocolloid can be gum *acacia* (i.e., gum Arabic), and the emulsifier can be quillaja extract.

DETAILED DESCRIPTION

These and other systems, methods, objects, features, and advantages of the present disclosure will be apparent to those skilled in the art from the following detailed description of the embodiments and drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from context.

A. Cannabinoids

Oral formulations of the present disclosure include at least one cannabinoid. The cannabinoids are a class of molecules primarily obtained through the extraction of *cannabis* plant material, although synthetic and/or bioreactor production, and or other methods may also be used to obtain or modify them. Various cannabinoids, used alone or in combination, have shown a variety of significant biological effects including but not limited to pain relief, anti-cancer, anti-inflammatory, anti-emetic, anti-convulsant, and many others, including recreational effects.

The cannabinoids include, but are not limited to THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran). Naturally occurring cannabinoids may be characterized by their type, such as Cannabigerol-type (CBG), Cannabichromene-type (CBC), Cannabidiol-type (CBD), Cannabinodiol-type (CBND), Tetrahydrocannabinol-type (THC), Cannabinol-type (CBN), Cannabitriol-type (CBT), Cannabielsoin-type (CBE), the Isocannabinoids, Cannabicyclol-type (CBL), Cannabicitran-type (CBT), and Cannabichromanone-type (CBCN). The chemical structures of a non-exhaustive list of cannabinoids, organized by type, are shown in TABLE 1.

TABLE 1

Exemplary plant cannabinoids by type.

Cannabigerol-type (CBG)

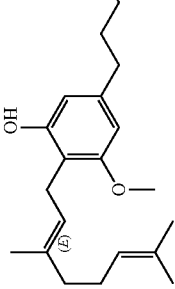
Cannabigerol
(E)-CBG-C$_5$

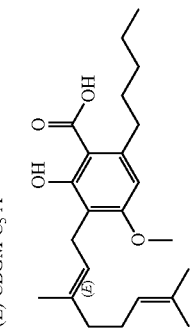
Cannabigerolic acid A
(E)-CBGA-C$_5$A

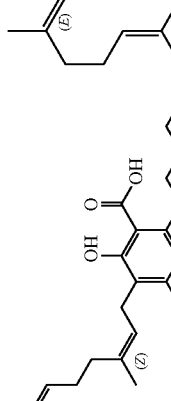
Cannabigerol monomethyl ether
(E)-CBGM-C$_5$A

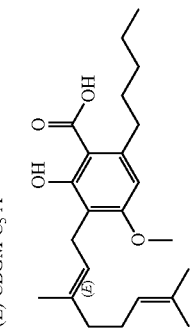
Cannabigerolic acid A monomethyl ether
(E)-CBGAM-C$_5$A

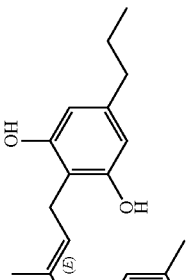
Cannabinerolic acid A
(Z)-CBGA-C$_5$A

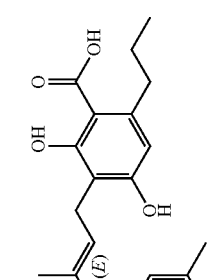
Cannabigerovarin
(E)-CBGV-C$_3$

Cannabigerovarinic acid A
(E)-CBGVA-C$_3$A

Cannabichromene-type (CBC)

(±)-Cannabichromene
CBC-C$_5$

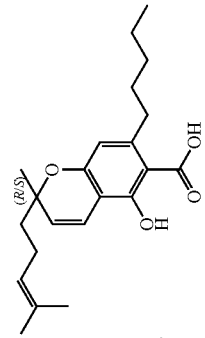
(±)-Cannabichromenic acid A
CBCA-C$_5$A

(±)-Cannabivarichromene, (±)-Cannabichromevarin
CBCV-C$_3$

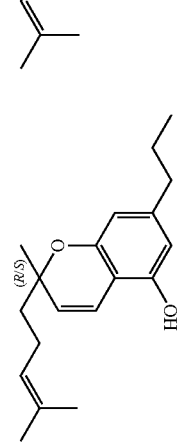
(±)-Cannabichromevarinic acid A
CBCVA-C$_3$A

TABLE 1-continued
Exemplary plant cannabinoids by type.
Cannabidiol-type (CBD)
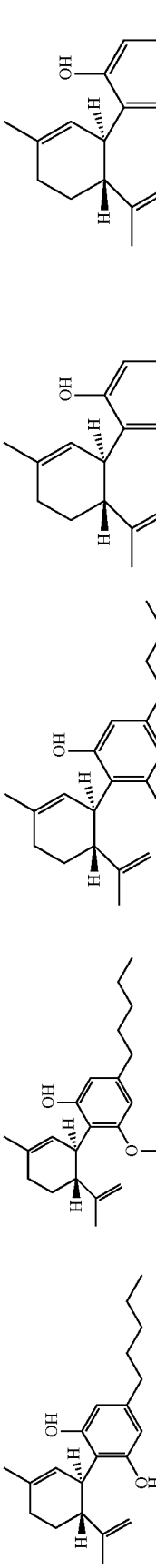
(−)-Cannabidiol
CBD-$C_5$
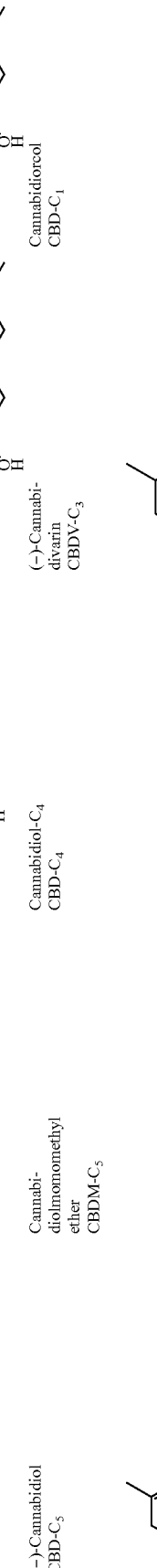
Cannabidiolic acid
CBDA-$C_5$
Cannabidiol monomethyl ether
CBDM-$C_5$
Cannabidiol-$C_4$
CBD-$C_4$
(−)-Cannabidivarin
CBDV-$C_3$
Cannabidivarinic acid
CBDVA-$C_3$
Cannabidiorcol
CBD-$C_1$
Cannabinodiol-type (CBND)
Cannabinodiol
CBND-$C_5$
Cannabinodivarin
CBND-$C_3$ TABLE 1-continued Exemplary plant cannabinoids by type.

Tetrahydrocannabinol-type (THC)

| Structure | Name |
|---|---|
| | Δ⁹-Tetrahydrocannabinol<br>Δ⁹-THC-C₅ |
| | Δ⁹-Tetrahydrocannabinolic acid A<br>Δ⁹-THCA-C₅ A |
| | Δ⁹-Tetrahydrocannabinolic acid B<br>Δ⁹-THCA-C₅ B |
| | Δ⁹-Tetrahydrocannabinol-C₄<br>Δ⁹-THC-C₄ |
| | Δ⁹-Tetrahydrocannabinolic acid-C₄ A and/or B<br>Δ⁹-THCA-C₄ A and/or B |
| | Δ⁹-Tetrahydrocannabivarin<br>Δ⁹-THCV-C₃ |
| | Δ⁹-Tetrahydrocannabivarinic acid A<br>Δ⁹-THCVA-C₃ A |
| | Δ⁹-Tetrahydrocannabiorcol<br>Δ⁹-THCO-C₁ |
| | Δ⁹-Tetrahydrocannabiorcolic acid A and/or B<br>Δ⁹-THCOA-C₁ A and/or B |
| | (−)-Δ⁸-trans-(6aR,10aR)-Tetrahydrocannabinolic acid A<br>Δ⁸-THCA-C₅ A |
| | (−)-Δ⁸-trans-(6aR,10aR)-Δ⁸-Tetrahydrocannabinol<br>Δ⁸-THC-C₅ |
| | (−)-(6aS,10aR)-Δ⁹-Tetrahydrocannabinol<br>(−)-cis-Δ⁹-THC-C₅ |

TABLE 1-continued

Exemplary plant cannabinoids by type.

Cannabinol-type (CBN)

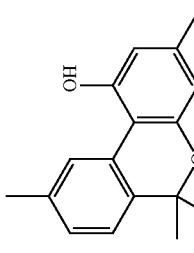
Cannabinol
CBN-C5

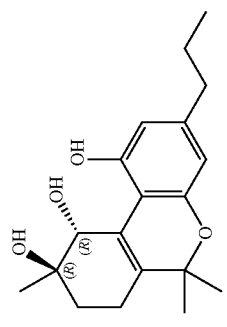
Cannabinolic acid A
CBNA-C5 A

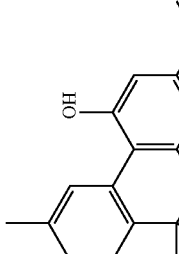
Cannabinol-C4
CBN-C4

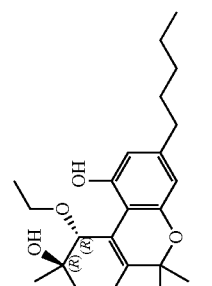
Cannabinol methyl ether
CBNM-C5

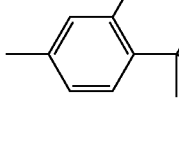
Cannabivarin
CBN-C3

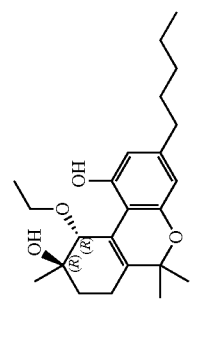
Cannabinol-C2
CBN-C2

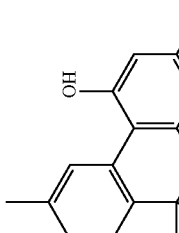
Cannabiorcol
CBN-C1

Cannabitriol-type (CBT)

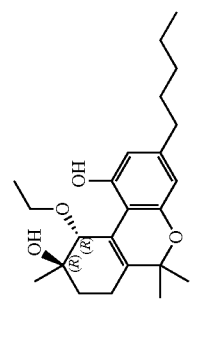
(−)-(9R,10R)-trans-Cannabitriol
(−)-trans-CBT-C5

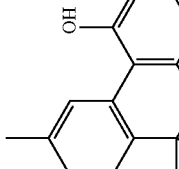
(+)-(9S,10S)-Cannabitriol
(+)-trans-CBT-C5

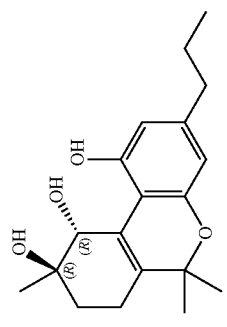
(±)-(9R,10S/9S,10R)-Cannabitriol
(±)-cis-CBT-C5

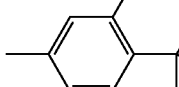
(−)-(9R,10R)-trans-10-O-Ethyl-cannabitriol
(−)-trans-CBT-OEt-C5

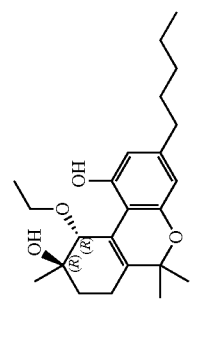
(±)-(9R,10R/9S,10S)-Cannabitriol-C3
(±)-trans-CBT-C3

TABLE 1-continued

Exemplary plant cannabinoids by type.

| 8,9-Dihydroxy-Δ$^{6a(10a)}$-tetrahydrocannabinol 8,9-Di-OH-CBT-C$_5$ | Cannabidiolic acid A cannabitriol ester CBDA-C$_5$ 9-OH-CBT-C$_5$ ester | (−)-(6aR,9S,10S,10aR)-9,10-Dihydroxy-hexahydrocannabinol, Cannabiripsol Cannabiripsol-C$_5$ | (−)-6a,7,10a-Trihydroxy-Δ$^9$-tetrahydro-cannabinol (−)-Cannabitetrol | 10-Oxo-Δ$^{6a(10a)}$-tetrahydrocannabinol OTHC |

Cannabielsoin-type (CBE)

| (5aS,6S,9R,9aR)-Cannabielsoin CBE-C$_5$ | (5aS,6S,9R,9aR)-Cannabielsoic acid A CBEA-C$_5$ A | (5aS,6S,9R,9aR)-Cannabielsoic acid B CBEA-C$_5$ B | (5aS,6S,9R,9aR)-C$_3$-Cannabielsoin CBE-C$_3$ | (5aS,6S,9R,9aR)-C$_3$-Cannabielsoic acid B CBEA-C$_3$ B |

TABLE 1-continued

Exemplary plant cannabinoids by type.

Cannabiglendol-C₃
OH-iso-HHCV-C₃

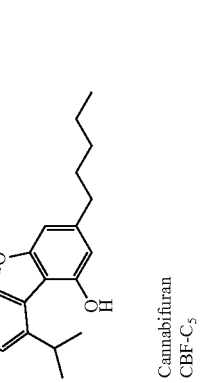
Dehydro-cannabifuran
DCBF-C₅

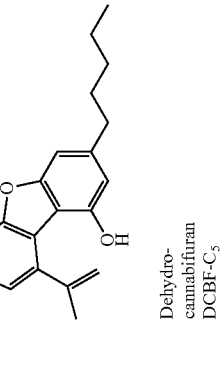
Cannabifuran
CBF-C₅

Isocannabinoids

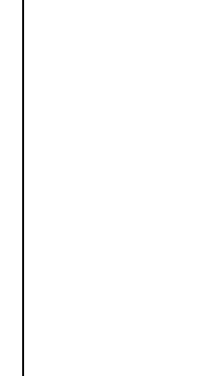
(−)-Δ⁷-trans-(1R,3R,6R)-Isotetrahydro-cannabinol

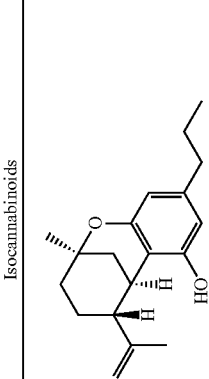
(±)-Δ⁷-1,2-cis-(1R,3R,6S/1S,3S,6R)-Isotetrahydro-cannabivarin
and (1S, 3S, 6R)

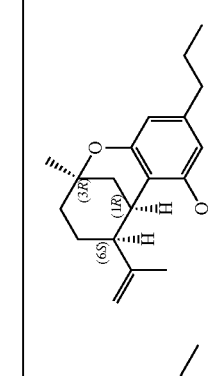
(−)-Δ⁷-trans-(1R,3R,6R)-Isotetrahydro-cannabivarin

Cannabicyclol-type (CBL)

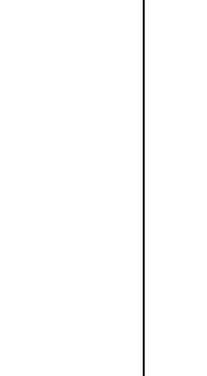
(±)-(1aS,3aR,8bR,8cR)-Cannabicyclol
CBL-C₅

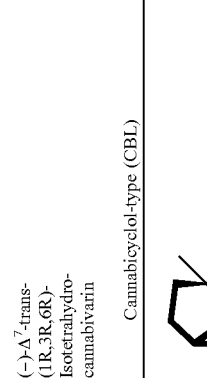
(±)-(1aS,3aR,8bR,8cR)-Cannabicyclolic acid A
CBLA-C₅ A (±)-(1aS,3aR,8bR,8cR)-Cannabicyclovarin
CBLV-C₃

TABLE 1-continued
Exemplary plant cannabinoids by type.
Cannabicitran-type (CBT)
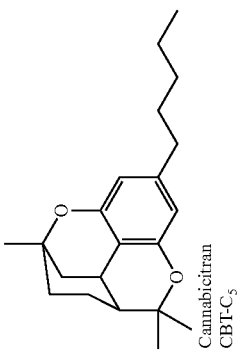
Cannabicitran
CBT-C$_5$
Cannabichromanone-type (CBCN)
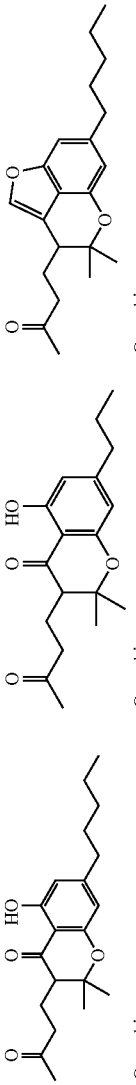
Cannabichromanone
CBCN-C$_5$
Cannabichromanone-C$_3$
CBCN-C$_3$
Cannabicoumaronone
CBCON-C$_5$ The at least one cannabinoids of the oral formulations can come from any source. In one or more embodiments, the cannabinoid is in the form of an extract from a *cannabis* plant. In some cases, the extract contains a full spectrum of phytochemicals (e.g., phytocannabinoids, terpenes, and phenylpropanoids). The extract can be a distillate or isolate comprising a select group of cannabinoids, or an individual cannabinoid.

In addition to naturally occurring cannabinoids, synthetic cannabinoids and derivatives thereof with cannabimimetic properties, include, but are not limited to rimonabant, JWH-018, JWH-073, CP-55940; dimethylheptyran; HU-210; HU-331, SR144528, WIN 55,212-2, JWH-133, Levonantradol (Nantrodolum), AM-2201, etc.

In some embodiments the extracts, preparations, or individual cannabinoids are used in their un-modified state. In some embodiments the cannabinoid/cannabinoid mixtures are processed to alter their physical properties according to methods known in the art. Exemplary processes include, the creation of emulsions, micro-emulsions, nano-emulsions, liposomes, micelles, colloids, encapsulations, complexation with solubility enhancers such as, for example, cyclodextrins, hydrocolloids, sugars, sugar alcohols, emulsifiers, surfactants, and the like.

In some cases, an oral formulation of the present disclosure includes at least one of: THC, THCA, CBD, CBDA, CBG, CBC, and THCV. In a particular embodiment, the formulations include THC and CBD. The ratio of THC:CBD can be any ration in the range of 1:100 to 100:1 or 1:50 and 50:1, such as 10:1, 1:1, and 1:10.

B. Other Active Ingredients:

In some embodiments, the oral cannabinoid formulation includes one or more added essential oils selected from Sweet Orange (*Citrus sinensis* spp), Peppermint (*Mentha piperita* spp), Lemon (*Citrus limon* spp), Lavender (*Lavendula angustifolia* spp) and Vanilla (*Vanilla planifolia* spp). In some embodiments, the *cannabis* oil extract includes Vitamin E and one or more essential oils selected from Sweet Orange (*Citrus sinensis* spp), Peppermint (*Mentha piperita* spp), Lemon (*Citrus limon* spp), Lavender (*Lavendula angustifolia* spp) and Vanilla (*Vanilla planifolia* spp).

Other essential oils that can be used in the compositions of the invention include, but are not limited to: Agarwood; Agarwood Attar; Ahibero; Allspice; Almond, bitter; Amber Oil; Ambrette Seed; Amyris; *Angelica* Root; *Angelica* Seed; Aniseed; Anise; Anise (star); Armoise (Mugwort); *Artemisia vestita*; Asafoetida; Bakul; Balsam of Peru Oil; Balsam of Peru Resin; Balsamite; Baobab Oil; Basil, Sweet ct Linalool; Basil, Sweet ct Linalool—Organic; Basil, Sweet ct Methyl Chavicol—Organic; Bay; Beeswax; Bergamot; Birch; Boldo; *Boronia*; Black Cumin; Black Currant Bud; Blue *Lotus Attar*; Broom; Buchu; *Bupleurum* (*Bupleurum fruticosum*); Buddha wood; Butter; Cabreuva; Cade; Cajuput; Calamus; *Calendula*; Camomile (or Chamomile); Camphor; *Cananga*; Cangerana; Cape Chamomile (*Ericephalus punctulatus*) S. Africa, Wild Harvest; Cape May; Caraway; Caraway; Cardamom; Carnation; Carrot Seed; Cascarilla; *Cassia*; Cassie; Catnip; Cedar (Cedrus) India; Cedarwood; Cedarwood, Atlas—Organic; Cedarwood, Himalayan; Cedarwood, Tex.; Cedarwood, Va.; Celery leaf; Celery Seed; Chamomile, Blue; Chamomile; Chamomile, Roman (*Anthemis nobilis*); Champa Attar (*Michelia champaca*) India; Champaca; Chaste tree; Cilantro; Cinnamon; Cinnamon Bark; *Cistus; Cistus* (*Cistus ladaniferus*) *Corsica; Citronella*; Clary Sage Absolute; Clary Sage, Bulgaria; Clary Sage, Russia; Clary Sage, USA; Clementine; Clove; Clove Bud; Cacao; Coconut Pulp; Coffee Bean Oil; Cognac, Green; *Coleus*; Combava (fruit or leaf); *Copaiba*; Coriander; Coriander Seed; Cucumber Hydrosol; Cumin; Cumin Seed; Cypress Leaf; Cypress, Blue; Davana; Dill; Elemi; *Eucalyptus*, Blue Gum; *Eucalyptus*, Blue Mallee; *Eucalyptus*, Lemon; Fennel (*Foeniculum vulgare*) Bulgaria; Fennel, Sweet; Fenugreek; Fern (sweet); Fleabane; Fir Needle; Fir, Balsam; Fir, Douglas; Fir, Silver; Fragonia; Frankincense, India; Frankincense, Somalia; Frankincense Frereana; Frankincense, Oman; Frankincense, Oman; Frankincense, Somalia; Galangal; Galbanum; Geranium; Geranium, Egypt; Geranium, Rose; Geranium, South Africa; Ghandi root; Ginger; Ginger Lily; Ginger, Fresh; Gingergrass (*Cymbopogon martinii*); Goldenrod; Grapefruit, Pink; Grapefruit, Ruby Red; Grapefruit, White; Hay; *Helichrysum, Albania; Helichrysum*, Croatia; Hina Attar, India; Hop; Hyssop *Decumbens*; Hyssop; Immortelle; *Jasmine* Absolute, Egypt; *Jasmine* Absolute, India; *Jasmine* Concrete; *Jasmine; Jasmine Sambac*; Jatamansi, (*Nardostachs jatamansi*); Juniper; Juniper Berry (*Juniperus communis*); Juniper Leaf/Berry; Kaffir Lime; Kava; Labdanum; Larch needle; Laurel (*Laurus nobilis*) *Corsica*; Laurel Leaf; Lavandin, Grosso; Lavender—High Elevation; Lavender—Wild; Lavender Absolute; Lavender Hydrosol; Lavender, Bulgaria; Lavender, France; Lavender, Maillette; Leleshwa; Lemon; Lemon Tea Tree; Lemon *verbena*; Lemongrass; Lentisque (*Pistacia lentiscus*) *Corsica*; Lime; Lime Essence Oil; Lime, Distilled; *Liquidambar* (*Styrax*); Longoza; *Lotus* Absolute, Pink; *Lotus* Absolute, White; Lovage leaf, Lovage root; *Magnolia* flower; Mandarin; Mandarin, Green; Mandarin, Red; Mandarin, Yellow; Mango ginger; Marjoram; Manila oil; *Melissa*; Mint; Mint, Himalayan (*Mentha arvensis*); Mitti Attar; Motia Attar (*Jasmine sambac*) India; Mugwort; Mustard; Myrrh; Myrtle, Green; Myrtle (*Myrtus Communis*); Nagarmotha (Cypriol); Neem (*Azadirachta indica*) India; Neroli; Niaouli; Nutmeg; Nut grass; Oakmoss Absolute; Oakwood; Opopanax, Sweet Myrrh (*Commiphora guidotti*); Orange, Blood; Orange, Sweet; Orange, Wild; Orange Blossom; Orange Essence Oil; Orange, Bitter Green; Orange, Bitter Red; Oregano; Orris Butter; Osmanthus Absolute; Palmarosa; Palmarosa, Nepal; Palmarosa, Sri Lanka; Palo Santo (*Bursera graveolens*); Palo Santo; Patchouli; Absolute; Patchouli, Dark; Patchouli, Light; Patchouli, Sri Lanka; Pennyroyal; Pepper, Black; Peppercorn, Pink; Peppermint, Chocolate; Peppermint, France; Peppermint, India; Peppermint, USA; Petitgrain Absolute; Petitgrain Bigarade; Petitgrain sur Fleurs; Petitgrain, Mandarin; Pimento; Pine; Pinion Juniper Co-distillation, Colorado, Wild Harvest; Pinon Pine (*Pinus edulis*) Colorado, Wild Harvest; Pitta blend (Lavender, Rose Geranium, Ruh Khus); Plai; Pomegranate Seed; *Rhododendron* (*Rhododendron anthopogon*); *Rhododendron* Leaf; Rosalina; Rose; Rose Attar; Rose de Mai Absolute; Rose de Mai Concrète; Rose de Mai Organic Extract; Rose geranium; Rose Hip Seed; Rose Otto, Bulgaria; Rose Otto, Turkey; Rose Otto, White—Organic; Rose vetiver; Rosemary Antioxidant; Rosemary ct Cineole; Rosemary ct Verbenone; Rosewood; Rue; Ruh Khus (*Vetiveria zizaniodes*); Saffron Attar, India; Sage; Samphire (*Cristhmum maritimum*) *Corsica*; Sandalwood; Sandalwood, New Caledonia; Sandalwood, Australian—Premium; Sandalwood (*Santalum spicatum*), Australia; Sandalwood Oil, Royal Hawaiian (*Santalum paniculatum*); Sandalwood, Royal Hawaiian; *Sassafras*; Savitri Rose Perfume; Sea Buckthorn; Seaweed; Sierra Juniper (*Juniperus occidentalis*); Spearmint; Spearmint (*Mentha Spicata*) Israel; Spikenard; Spikenard, Green; Spruce, Black; Spruce (*Picea mariana*) Canada; St. John's Wort 2; St. John's Wort (*Hypericum perforatum*) Bulgaria;

Tagetes; Tamanu (Foraha) Oil; Tangelo; Tangerine; Tangerine Murcott; Tansy; Tansy, Blue; Tarragon; Tea Tree; Tea Tree (*Leptospermum citratum*), Lemon Scented; Tea Tree (*Melaleuca alternifolia*) South Africa; *Thuja*; Thyme; Thyme ct Linalool; Tobacco; Tonka Bean; Tuberose; Tulsi, Holy Basic Oil (*Ocimum sanctum*); Turmeric; *Vanilla; Vanilla* Bourbon; *Verbena*; Vetiver—Double Distilled; Vetiver, El Salvador; Vetiver, Haiti; Vetiver, Sri Lanka; Violet Leaf; White Fir (*Abies concolor*); White *Lotus Attar*; White Sage (*Salvia apiana*); Wild Carrot, Corsica; Wintergreen; Wintergreen; Yarrow; Yarrow, Blue; Ylang; Yuzu; and combinations thereof.

The compositions of the invention can also include one or more herbal extracts of Abas, Abele, *Abies balsamea*, Absinthe, *Absinthium, Acacia, Acacia* spp., Acai Berries, Acerola, *Achillea millefolium*, Achiote, Aconite, *Aconitum napellus*, Acorns, Acorns calamus, Acorns gramineus, *Adansonia digitata*, Adder's Mouth, Adderwort, *Adiantum capillus*-veneris, *Aesculus hippocastanum, Aframomum melegueta*, African Geranium, African Ginger, *Agastache foeniculum*, Agave, *Agnus castus, Agrimonia eupatoria*, Agrimony, *Agropyron repens*, Ague Grass, Ague Root, Ague Tree, Agueweed, Ajamoda, Ajave Seeds, Ajenjo, *Ajowan, Ajuga reptans, Ajvain, Ajwan, Ajwain, Akebia, Akebia quinata*, Alaskan *Ginseng, Alchemilla vulgaris, Alchornea* Species, Alder, Alder Buckthorn, Alder Dogwood, Alecost, Alehoof, *Aletris, Aletris farinosa*, Alexandrian Laurel, Alexandrian *Senna*, Alfalfa, Algarroba, Alkanet, Allheal, Alligator Pepper, *Allium cepa, Allium porrum, Allium sativum, Allium schoenoprasum, Allium tuberosum*, Allspice, Almond, *Alnus glutinosa, Alnus rubra, Aloe ferox*, Aloeroot, Aloes, *Aloe* Vera, *Aloysia triphylla*, Alpine Strawberry, *Alpinia officinarum, Althaea, Althaea officinalis*, Aluka, Alumroot, *Amara aromatica, Amaracus*, Amaranth, *Amaranthus* Hypocondriacus, Amber Touch-and-heal, Ambroise, Ambrose, Amburana, America-Hodoimo, American *Aloe*, American *Angelica*, American Ash, American Aspen, American Basswood, American Bayberry, American Bee Balm, American Beech, American Bugleweed, American Carob, American Cranesbill, American Cress, American Dill, American Dogwood, American *Ginseng*, American Ground Lily, American Groundnut, American Linden, American Mandrake, American *Melissa*, American Saffron, American Sanicle, American Sarsaparilla, American Sloe, American Spikenard, American Upland Cotton, American Valerian, American Winter Cress, American Wormroot, American Wormseed, Amla, Ammi Visnaga, *Anacardium Occidentale, Ananas Comosus, Anchusa officinalis*, Andiroba, *Andrographis, Andrographis paniculata, Anemone, Anemone pulsatilla, Anemopsis californica, Anethum graveolens, Angelica, Angelica archangelica, Angelica sinensis, Angelica* Tree, *Angostura, Angostura trifoliata*, Anise, Aniseed, Aniseed Stars, Anise Fern, Anise Hyssop, Anise Plant, Annatto, *Annona muricata, Annona reticulata*, Annual Marjoram, *Anthemis nobilis, Anthoxanthum nitens, Anthriscus cerefolium*, Antilles Cherry, Apios americana, *Apium graveolens*, Apple, Apple Mint, Apple-of-Peru, Apricot Vine, Apsidium, *Aralia racemosa*, Arbe a suif, Arberry, Arboloco, Arbor Vitae, *Arbutus, Arbutus menziesii, Arbutus uva ursi*, Archangel, Archangelica, *Archangelica officinalis, Arctium lappa, Arctostaphylos uva ursi*, Ardraka, Argan, *Argania, Argania spinosa, Argemone mexicana*, Argentine, *Aristolochia serpentaria, Aristotelia chilensis*, Aritha, Arjaka, *Arjuna, Armoracia rusticana*, Armstrong, *Arnica, Arnica* Flowers, *Arnica montana, Arnica* Root, Aromatic Sumac, Aromatic Wintergreen, Arrowroot, *Artemisia, Artemisia abrotanum, Artemisia absinthium, Artemisia capillaris, Artemisia dracunculus, Artemisia tridentata, Artemisia vulgaris, Artocarpus altilis, Artocarpus heterophyllus*, Arugula, Asafoetida, *Asclepias tuberosa*, Ascophyllum nodosum, Ash, Ashwaganda, Asian *Ginseng*, Aspalathus *Linearis, Asparagus cochinchinensis, Asparagus racemosus, Asparagus* Root, *Asperula odorata*, Aspilia, Aspilia mossambicensis, Ass-ear, Asthma Plant, Asthma Weed, *Astragalus, Astragalus membranaceus, Atropa belladonna*, Auld Wife's Huid, Autumn *Crocus, Avena sativa*, Avens, Averrhoa carambola, Avocado, Ayak chichira, Ayuk Willku, *Azadirachta indica*, Azafran, Babchi Seeds, Bacc, Bachelor's-button, *Bacopa Monniera*, Bahama Berry, Baical Skullcap, Bai Guo, Bai Mu Erh, Ba Ji Tian, Baldina, Balinghoy, *Ballota nigra*, Balm Mint, Balm of Gilead, Balmony, Balsam *Copaiba*, Balsam Fir, Balsam of Gilead, Balsam of Peru, Balsam Tree, Bank Cress, *Banisteriopsis caapi* vine, Baobab, *Baptisia, Baptisia tinctoria*, Barbados *Aloe*, Barbados Cherry, *Barbarea verna*, Barberry, Barbary Fig, Bardana, Barley, Barosma Betulina, Barren Strawberry, Baran, Basil, Basil Thyme, Basin Sagebrush, Basketbush, Basswood, Bastard Cardamom, Bastard Saffron, Bast Tree, Bauple Nut, Bayawas, Bayberry, Bayberry Bush, Bayberry Wax Tree, Bay Laurel, Beaked Parsley, Bean of India, Bean Trefoil, Bearberry, Bearbind, Beard Lichen, Bear's Foot, Bear's-grape, Bear's-paw, Bear's Weed, Beaumont Root, Beauty Leaf, Bee Balm, Bee Bread, Beech, Beechdrops, Beech Wheat, Bee Plant, Bee Sage, Bee's Nest, Beggar's Buttons, *Belladonna*, Belle Isle Cress, Bellyache Root, Benjamin Bush, Benzoin Gum, Benzoin Tree, Berberidis, *Berberis Aquifolium, Berberis vulgaris*, Berberry, Bergamot Mint, Bergamot Orange, *Bertholletia wxcelsa, Betel*, Bethroot, Betony, *Betula alba, Betula pendula*, Bhang, Bian Xu, Bible Hyssop, Bible-leaf, Big Sagebrush, Bilberry, Billygoat Clover, Biltmore Ash, Bindweed, Bird's-foot, Bird's Nest, Birthroot, Birthwort, Biscuits, Bishop\'s Weed, Bistort, Bitter *Aloe*, Bitter Ash, Bitter Bark, Bitter Dock, Bitter Leaf, Bitter Melon, Bitter Nightshade, Bitter Orange, Bitter Orange Peel, Bitter Quassia, Bittersweet, Bitter Trefoil, Bitter Wood, Bitterworm, *Bixa orellana*, Black Alder, Black Alder Tree, Blackberry, Black Cherry, Black Choke, Black Chokeberry, Black Cohosh, Black Cohush, Blackcurrant, Black Dogwood, Black Ginger, Black Haw, Black Henbane, Black Horehound, Black Locust, Black Mustard, Black Pepper, Black Root, Black Sampson, Black Sanicle, Black Snakeroot, Black Stinking Horehound, Black Tany, Blackthorn, Black Thyme, Black Walnut, Black Whortleberry, Blackwort, Bladder Cherry, Bladder Fucus, Bladderpod, Bladderwrack, Blazing Star, Blessed Herb, Blessed Thistle, Blind Nettle, Bloodroot, Blood Vine, Bloodwort, Blooming Sally, Blow Ball, Blue Balm, Blueberry, Bluebottle, Blue Cohosh, Blue Curls, Blue Dandelion, Blue Flag, Blue Giant Hyssop, Blue *Ginseng*, Blue Gum, Blue Gum Tree, Blue *Iris*, Blue Mountain Tea, Blue Pimpernel, Blue Rocket, Blue-Sailors, Blue Skullcap, Blue Violet, Blunt-leaved Dock, Bodhi Tree, Bofareira, Bogbean, Bo He, Bola, Boldina, Boldo, Boldoa, Boldu, Boldus, Boneset, Bookoo, Borage, *Borago officinalis*, Boswellia carteri, Bo-Tree, Bottlebrush, Bouncing Bet, Bourtree, Bowman's Root, Boxberry, Boxwood, Brahmi, Bramble, Brandy Mint, *Brassica alba, Brassica juncea, Brassica nigra, Brassica oleracea, Brassica rapa Pekinensis*, Brazilian *Ginseng*, Brazil Nut, Breadfruit, Bread Wheat, Bride's Button, Bridewort, Brigham Tea, Brindall Berry, Brindle Berry, Brinton Root, British Myrrh, Broad-leaved Dock, Bromelain, Brook Bean, Brooklime, Broom, Broom Flowers, Broom Tops, Broom Tea-Tree, Brown Mustard, Brownwort, Bruisewort, Bryonia Alba, Bryony, Buchu, Buckbean, Buckeye, Buckler-leaved Sorrel, Buckthorn, Buckwheat, Bucku, Buddha Fruit, Buffalo Herb, Bugbane, Bugbane Squawroot, Bugle, Bugleweed, Bugloss, Bu Gu Zhi, Bugwort, Bull Flower, Bullock's Heart, Bull's Heart, Bunny's Ears, *Bupleurum, Bupleurum Chinese*, Bur, Burage, Burdock, Burdock Burrs, Burren Myrtle, Burr Marigoldt, Burrs, Burr Seed, Bush Nut, Butcher's Broom, Butterbur, Butterfly Weed, Butternut, Butter Winter, Butterwort, Butterweed, Buttons, Caban Cherry, Cabbage, Cabbage Palm, Cabbage Rose, Cacao, Cacari, Cajeput Tree, Cajueiro, Calabar Bean, Calamint, Calamintha *Nepeta*, Calamus, *Calendula, Calendula officinalis*, California Poppy, *Calluna vulgaris*, Calophyllum inophyllum, Caltrop, Calumba, Cambodian Mint, Camel Grass, Cammellia *Sinensis*, Camocamo, Camphor, Camphor Tree, Camptotheca *Acuminata*, Camu, Canabis, Canada Balsam, Canada Root, Canada Tea, Canadian Fleabane, Canaigre, *Cananga odorata*, Cancerosa, Caner Root, Cancer Tree, Candle Berry, Cane Ash, Canistel Fruit, Cankerwort, *Cannabis Sativa*, Cape *Aloe*, Cape Gooseberry, Caperberry, Caperbush, Capers, Capon's Tail, *Capparis spinosa, Capsaicin, Capsella Bursa-Pastoris, Capsicum, Capsicum Annuum, Capsicum chinense, Carambola, Carapa guianensis*, Caraway, Caraway Seed, Cardamom, Cardamom Seeds, Cardamon, *Carduus marianus, Carica Papaya*, Carob, Carolina *Jasmine*, Carom, Carony Bark, Carpenter's-herb, Carpenter's-square, Carpenter's Weed, Carrageen, Carrot, Carthamus Tinctorius, *Carum Carvi*, Cascara, Cascara Buckthorn, Cascara Sagrada, Caseweed, Cashew Nut Shells, Cassava, *Cassia Senna, Castanea Sativa*, Castor Bean Plant, Castor Oil Plant, Catalonian *Jasmine*, Catchweed, Catha, Catha *Edulis*, Catmint, Catnep, Catnip, Catrup, Cat's Claw, Cat's-foot, Cat's-play, Catswort, Cat Thyme, Catuaba, *Caulophyllum thalictroides*, Cayenne, *Ceanothus americanus*, Cedar Nut, Celandine, Celery, *Centaurea cyanus, Centaurium erythraea*, Centaury, *Centella asiatica*, Century Plant, Cephaelis Ipecacuanha, Cerasee, *Ceratonia Siliqua*, Cereso, *Cetraria islandica*, Chaga Mushroom, Chai Hu, *Chamaelirium luteum*, Chamomile, Chanca *Piedra*, Chandan, Chang Pu, Chaparral, Charapilla, Chaste Berry, Chaste Tree, Chat, Chaulmoogra, Checkerberry, Cheeseflower, Cheese Rennet, Cheiranthus *Cheiri, Chelidonium Majus*, Chelone *Glabra, Chenopodium Ambrosioides*, Chen-Pi, Cherry Birch, Chervil, Chia, Chian, Chien, Chiang, Chickweed, Chicory, Chihma, Chi-hsueh-ts'ao, Chilean Wineberry, Chilgoza, Chili Pepper, Chimaphila *Umbellata*, China Root, Chin-ch'iao-mai, Chinese *Angelica*, Chinese Cabbage, Chinese Chives, Chinese Foxglove, Chinese *Ginseng*, Chinese Gold Thread, Chinese Lantern, Chinese Licorice, Chinese Mustard, Chinese Nettle, Chinese Star Anise, Chinese Wolfberry, Chink, *Chionanthus Virginicus*, Chirayata, Chiretta, Chittembark, Chives, Chocolate, Chocolate Root, Chocolate Vine, Choke Cherry, Chondrus *Crispus*, Christmas Tree, *Chrysanthemum, Chrysanthemum Balsamita, Chrysanthemum Cinerariifolium, Chrysanthemum Morifolium*, Chuan Xin Liang, Chuchupate, Church Steeples, Cicely, *Cichorium Intybus*, Cilantro, Cimicifuga, Cimicifuga *Racemosa*, Cinchona, Cinchona Bark, Cinchona spp, Cingulum Sancti *Johannis*, Cinnabar Root, *Cinnamomum Camphora, Cinnamomum Zeylanicum*, Cinnamon, Cinnamonwood, Cinquefoil, *Cirsium Vulgare*, Citroengrass, *Citrus aurantium, Citrus bergamia, Citrus ichangensis* x *Citrus reticulata* var. *austera, Citrus limon, Citrus reticulata, Citrus thyme*, City Avens, Clary, Clary Sage, Clear Eye, Cleavers, *Clematis* Stem, Clove, Clove Garlic, Clover, Clover Broom, Clove Root, Clown's Woundwort, Clubfoot Moss, Club Moss, *Cnicus Benedictus*, Coca, Coca Shrub, Cocasheed, *Cochlearia officinalis*, Cocklebur, Cockle Buttons, Cocoa, *Codonopsis, Codonopsis pilosula, Coffea arabica*, Coffee, Coffeeweed, Coicis, *Coix, Coix* Lachryma-jobi, Cola *nitida, Colchicum, Colchicum Autumnale, Coleus, Coleus* Forkolil, *Coleus Forskohlii*, Colewort, Colicroot, Colla, Collinsonia *canadensis*, Colorado Cough Root, Coltsfoot, Colt's-tail, Comfrey, *Commiphora* Molmol, *Commiphora Mukul, Commiphora* Opobalsamum, Common Alder, Common Alkanet, Common Anise, Common *Arnica*, Common Ash, Common Balm, Common Barberry, Common Basil, Common Blue Violet, Common Broom, Common Buckthorn, Common Buckwheat, Common Bugle, Common Burnet, Common Caraway, Common Centaury, Common Chamomile, Common Club Moss, Common Cotton, Common Dock, Common Dill, Common Fennel, Common Fenugrec, Common Flax, Common Foxglove, Common Hazel, Common Holly, Common Hop, Common Horehound, Common Hyssop, Common *Jasmine*, Common Juniper, Common Lavender, Common Lime, Common Madder, Common Mallow, Common Marjoram, Common Nettle, Common Oats, Common Onion, Common Parsley, Common Periwinkle, Common Privet, Common Rue, Common Sage, Common Sagebrush, Common Sea-Buckthorn, Common Stinging Nettle, Common Strawberry, Common Sundew, Common Thistle, Common Thyme, Common Wheat, Common White *Jasmine*, Common Willow, Common Wormwood, Compass Plant, Compass Weed, Compositae, *Conium Maculatum*, Consormol, Consumptive's Weed, *Convallaria Majalis, Convolvulus Sepium*, Cool Tankard, *Copaiba, Copal, Copaifera* Species, *Coptidis, Coptis, Coptis chinensis, Coptis* Rhizome, *Cordyceps, Cordyceps sinensis*, Coriander, *Coriandrum sativum*, Corn, Cornelian Tree, Cornflower, Cornish Lovage, Corn Mint, Corn Poppy, Corn Rose, Cornsilk, *Cornus florida*, Corsican Mint, Corsican Pepper, Corydalis, Corydalis Rhizome, Corydalis Yanhusuo, *Corylus avellana*, Costmary, Cotton, Cotton Thistle, Couch Grass, Coughroot, Coughweed, Coughwort, Countryman's-treacle, Cowbloom, Cow Chervil, Cow Clover, Cow Cress, Cowgrass, Cowplant, Cowslip, Crampbark, Crampweed, Cranberry, Cranberry Bush, Cranberry Tree, Cranesbill, *Crataegus* Monogyna, *Crataegus Oxyacantha*, Crataeva, Crataeva nurvula, Cream Of Tartar Tree, Creathnach, Creeping Charlie, Creeping Thyme, Creosote Bush, *Crocus sativus*, Crosswort, Croton Lechleri, Crowberry, Crow Corn, Cuban Oregano, Cubeb Pepper, Cuckoo's Cap, *Cucurbita Pepo*, Culantrillo, Culver's Physic, Culver's Root, Cumaru, Cumaruzeiro, Cumin, *Cuminum cyminum*, Curacao *Aloe*, Curare, *Curcuma longa, Curcuma zedoaria*, Cure-all, Curled Dock, Curled Mint, Curly Parsley, Curry-leaf tree, Curry Tree, Cuscus, Cuscuta Epithymum, Cusparia Bark, Custard Apple, Cutleaf Bugleweed, Cutweed, *Cydonia Oblonga, Cymbopogon* Citratus, *Cypripedium Pubescens*, Da Huang, Dalcini, Dalmatian *Iris*, Dalmation Insect Flower, Dalmation Pellitory, Dalmatian Sage, Damiana, Dandelion, Dang Gui, Danish Dill, Dan Shen, Daruharidra, Da suan, *Datura Stramonium, Daucus carota*, Deadly Nightshade, Deadmen's Bells, Dead Nettle, Dead-Rat Tree, Death-flower, Deerberry, Desert Cactus, Desert Oregano, Desert Tea, Devil's-apple, Devil's Bit, Devil's-bones, Devil's Cherries, Devil's Claw, Devil's Club, Devil's Dung, Devil's-eye, Devil's Guts, Devil's Herb, Devil's Plague, Dew of the Sea, Dhup, *Digitalis Purpurea*, Di Huang, Dill, Dillisk, Dillseed, Dillweed, Dilly, Dilsk, Dilo Oil Tree, *Dioscorea Villosa*, Diosma Betulina, Dipsacus *Sylvestris, Dipteryx Odorata*, Divale, Djamboe, Doda, Dodan, Doadni, Dodder, Dog Brier, Dog Grass, Dog Rose, Dog's Mercury, Dog Tree, Dogwood, Dong Chong Xia Cao, Dong Quai, Dovefoot, Drago, Dragon's Blood, Dragon's mugwort, Dragonwort, Dropsy Plant, Drosera *Rotundifolia*, Dryopteris filix-mas, Ducks Foot, Dulse, Dutch Clover, Dwale, Dwarf Juniper, Dwarf Nasturtium, Dwayberry, Dyeberry, Dyer's Broom, Dyer's Greenweed, Dyer's Madder, Dyer's-saffron, Dysphania *ambrosioides*, Early Winter Cress, Earthsmoke, Easter Flower, Easter Giant, Eau-de-cologne Mint, *Echinacea, Echinacea Angustifolia*, Egg Fruit, Egg Wrack, Egyptian Privet, Eight-horned Anise, Eight-horns, Ela, Elaci, Elder, Elder-berry, Elder-flower, Elecampane, Eletteria Cardamomum, Eleuthero, Eleutherococcus Senticosus, Elk Mint, Emetic Herb, Enandi, Endive, English Alder, English Balm, English Catnip, English Chamomile, English Hawthorn, English Holly, English Hop, English Mandrake, English Serpentary, English Thyme, English Valerian, English Violet, English Wallflower, Epazote, Ephedra, Ephedra *Nevadensis*, Ephedra *Sinica*, Epifagus *virginiana*, Epilobium *Angustifolium*, Epimedium, Epimedium *grandiflorum*, Equisetum *Arvense*, Erigeron *canadensis*, Eriodictyon *Californicum, Eruca vesicaria sativa*, Erythraea *Centaurium*, Erythroxylum Catuaba, Erythroxylum Coca, *Eschscholzia Californica*, Espinheira Santa, Estragon, Ethiopian Cumin, *Eucalyptus, Eucalyptus Globulus*, Eugenia Carophyllata, Eupatorium, Eupatorium *Perfoliatum*, Eupatorium *Purpureum, Euphorbia Hirta*, Euphrasia *officinalis*, European Alder, European *Angelica*, European Ash, European Barberry, European Black Alder, European Buckthorn, European Centaury, European Chestnut, European Cowslip, European Dill, European Elder, European Holly, European Hop, European White Water lily, European Willow, *Euterpe Oleracea*, Evening Primrose, Evening Star, Evergreen, Eye Balm, Eyebright, Eyeroot, *Fagopyrum Esculentum, Fagus* Grandifalia, Fah Tolai, Fairy Cup, Fairy's Glove, False *Acacia*, False Box, False Chamomile, False *Jasmine*, False Saffron, False Unicorn, False Valerian, False White Cedar, Featherfew, Featherfoil, Feather Geranium, Febrifuge Plant, Felon Herb, Felonwort, Female Fern, Fennel, Fenugreek, Ferula Asafoetida, Fetid Horehound, Fever Bush, Feverfew, Fever Grass, Fever Tree, Feverwort, Fiber, *Ficus* religiosa, Field Balm, Field Pansy, Field Poppy, Field Pumpkin, Field Sorrel, Figwort, Filipendula Ulmaria, Fir, Fir Balsam, Fireweed, Fir Pine, Fishfuddle, Five-fingers, Five-leaf, Flag Lily, Flagroot, Flanders Poppy, Flannelleaf, Flat-leaved Parsley, Flax, Flax Seed, Flax Weed, Fleabane, Flea Seed, Flesh and Blood, Fleur-de-lis, Flinders Rose, Florentine *Iris*, Florida Dogwood, Florida Fishpoison Tree, Flower de-luce, Flowering Dogwood, Flowering Willow, Flowery Knotweed, *Foeniculum Vulgare*, Folk's Glove, Food Of The Gods, Forsythia, Forsythia suspensa, Fo Ti, Foxberry, Fox Geranium, Foxglove, Fox Grape, Foxtail, *Fragaria ananassa, Fragaria vesca*, Fragrant Balm, Fragrant Giant Hyssop, Fragrant Sumac, Frankincense, *Fraxinus Americana, Fraxinus Excelsior*, French Basil, French Lilac, French Parsley, French Rose, French Sorrel, French Tarragon, French Thyme, Friar's Cap, Fringe Tree, *Fritillaria, Fritillaria Thunbergii*, Frog Plant, Fucus Vesiculosus, Fu-ling, Fuller's-herb, Fumaria *officinalis*, Fumitory, Gagroot, Galangal, Galega *officinalis*, Galipea *officinalis, Galium Aparine, Galium Odoratum, Galium Verum*, Gambooge, Gan cao, Gandana, Ganja, Gan Jiang, *Ganoderma Lucidum*, Gao Liang, Garabato, Garcinia, Garcinia cambogia, Garcinia gummi-gutta, Garcinia Kola, Garden *Angelica*, Garden Balm, Garden Basil, Garden Burnet, Garden Chamomile, Garden Chervil, Garden Chicory, Garden Dill, Garden Heliotrope, Garden Hyssop, Garden Lavender, Garden Loosestrife, Garden Marigold, Garden Mint, Garden Myrrh, Garden or Green Purslane, Garden Patience, Garden Rosemary, Garden Rue, Garden Sage, Garden Thyme, Garden Violet, Garlic, Garlic Chives, Garlic Sage, *Gaultheria Procumbens*, Ge-gen, *Gelsemium sempervirens, Genista, Genista Tinctoria, Gentian, Gentiana Lutea*, Geranium *Maculatum*, Geranium *Robertianum*, Geraniums, German Chamomile, Germander, German Mustard, German Rue, German Tarragon, German Thyme, German Valerian, *Geum urbanum*, Ghaap, Gill Run Over, Ginger, *Ginkgo, Ginkgo Biloba, Ginkgo* Nut, Ginny Grains, Ginny Papper, *Ginseng, Glechoma Hederacea*, Glossy Buckthorn, *Glycine max, Glycyrrhiza Glabra*, Goathead, Goat's Rue, Goatweed, Goat Wort, Gold Coin Grass, Golden Aspen, Goldenberry, Golden Flower of Mary, Golden Loosestrife, Golden Ragwort, Golden Root, Goldenrod, Goldenseal, Golden *Senecio*, Gold *Melissa*, Goldy Star, Goosefoot, Goose Grass, Goosewort, Gorikapuli, Gospel Tree, *Gossypium Hirsutum*, Gotu Kola, Gourmet Parsley, Goutweed, Gow Choy, Graines, Grains Of Paradise, Gramineus, Grape, Grape Vine, Grass, Grass Burdock, Gravelroot, Graviola, Graybeard, Greasewood, Great Burdock, Greater Burnet, Greater Cardamom, Great Morel, Great Nettle, Great Stinging Nettle, Great Wild Valerian, Greek Hayseed, Green Ginger, Green Ozier, Green Tea, *Grifola frondosa*, Grindelia, Grindelia Camporum, Groats, Ground Berry, Ground Cherry, Ground Holly, Ground Ivy, Ground Juniper, Ground Lemon, Ground Lily, Groundnut, Ground Pine, Ground Raspberry, Grouse Berry, Guaiac, *Guaiacum*, Guajacum, *Guaiacum officinale, Gualtheria procumbens*, Guarana, Guasai, Guava Tree, Guelder Rose, Guggul, Gui, Guinea Grains, Guinea Pepper, Guinea Seeds, Gum Bush, Gum Guggulu, Gum Myrrh Tree, Gumplant, Gurmabooti, Gurmar, *Gymnema, Gymnema sylvestre*, Gynostemma, Gynostemma pentaphyllum, Gypsyweed, Gypsywort, Habanero Pepper, Hackmatack, Hai-ts'ao, *Hamamelis Virginiana*, Handflower, Happy Tree, Hapusha, Hardock, Hareburr, Hare's Ear Root, *Harpagophytum procumbens*, Hartshorn Plant, Harvest Lice, Hasabis, Hashish, Hatomugi, Haw, Hawaii Nut, Hawkweed, Hawthorn, Haymaids, Hazelnut Tree, Heal-All, Heart Of The Earth, Heartsease, Heather, *Hebanthe paniculata*, Hedge Bind Weed, Hedge Fumitory, Hedge Maid, Hedlondilla, *Helianthus annuus*, Heliotrope, Hellweed, Helmet Flower, Helonias Root, Hemlock, Hemp, Henbane, Henna, Herb Bennet, Herb-of-Grace, Herb of St. Barbara, Herb of The Angels, Herb-of-the-cross, Herb Robert, Hercules Woundwort, He Shou Wu, *Hibiscus, Hibiscus Sabdariffa, Hieracium* Pilosella, *Hierochloe odorata*, High *Angelica*, High Mallow, Hill Berry, Hina, Hind Heal, Hineheel, Hing, Hini, Hippophae rhamnoides, Hip Rose, Hoarhound, Hock-heal, Hodoimo, Hoelen, Hog Apple, Hog Bean, Hog Cranberry, Hogweed, Holigold, Holly, Holy Basil, Holy Ghost Plant, Holy Herb, Holy Grass, Holy Thistle, Honey Plant, Honeysuckle, *Hoodia, Hoodia pilifera*, Hood Weed, Hoodwort, Hook-heal, Hopniss, Hops, Hops Vine, Horehound, Horny Goatweed, Horse Balm, Horse Chestnut, Horsefly Weed, Horseheal, Horse Mint, Horseradish, Horse Savin, Horsetail, Horse Thistle, Horseweed, Ho She Wu, Ho Shou Wu, Hot Mint, Hsia-ku-ts'ao, Hsiao-hui-hsiang, Hsieh-tzu-ts'ao, Hua-Hsian, Huang Qi, Huang Quin, Huarango, Hu-chin-ts'ao, Huckleberry, Hu-lu-ba, Hu-lu-pa, *Humulus lupulus*, Hungarian Chamomile, Huo Ma Ren, Hurrburr, Hurtleberry, Hurtsickle, Husk Cherry, *Hydnocarpus, Hydnocarpus kurzii, Hydrangea, Hydrangea Arborescens*, Hydrastis *canadensis, Hyoscyamus Niger, Hypericum, Hypericum* Perforatum, Hyssop, *Hyssopus officinalis*, Iceland Lichen, Iceland Moss, I-chi-kao, Ignatia *Amara*, Ignatius Bean, llang-Ilang, *ilex Aquifolium, ilex Paraguariensis, Illicium verum*, Ill-scented Sumac, Imburana De Cheiro, Incensier, Indian Apple, Indian Arrowroot, Indian Balm, Indian Balmony, Indian Bedellium, Indian Borage, Indian Bread, Indian Chickweed, Indian Corn, Indian Dye, Indian Elm, Indian Gentian, Indian *Ginseng*, Indian Gooseberry, Indian *Lotus*, Indian Mustard, Indian Nettle, Indian Nut, Indian Olibanum, Indian Paint, Indian Pennywort, Indian Pink, Indian Plant, Indian Plume, Indian Potato, Indian Red Paint, Indian Root, Indian Sage, Indian Shamrock, Indian Snakeroot, Indian Tobacco, Indian Tree, Indigo Broom, Inonotus obliquus, Inula Helenium, Ipecac, Ipecac Shrub, Ipio, Iporoni, Iporuru, *Iris, Iris* Florentina, *Iris Germanica*, Irish Broom, *Iris pallida*, Irish Moss, *Iris Versicolor*, Italian Burnet, Italian Cress, Italian *Jasmine*, Italian Lovage, Italian Pimpernel, Ivory Plum, Jaborandi, Jackfruit, Jack Tree, Jak, Jacob's Chariot, Jacob's-staff, Jacon, Jamaican Dogwood, Jamaica Pepper, Jamaica Sorrel, Jambu, Jambul, Jamestown Weed, Japanese Catnip, Japanese Grapefruit, Japanese Horseradish, Japanese Mint, Japanese Mushroom, Japanese Seaweed, Jasmin, *Jasmine*, Jasmini Flos, *Jasminum* spp., Jateorhiza *Palmata*, Jaundice Berry, Jaundice Root, Java Pepper, Java Plum, Jersey Tea, Jerusalem Oak, Jessamine, Jesuit's Balsam, Jesuit Tea, Jew's-harp Plant, Jiaogulan, Jicara, Jimsonweed, Jing Jie, Jin Qian Cao, Jin Yin Hua, Job's Tears, Joe Pye Weed, *Juglans cinerea, Juglans nigra, Juglans Regia*, Johnny-jump-up, Johnswort, Joint Fir, Ju Hua, Juniper, Juniper Bark, Juniper Berry, Juniper Bush, Jupiter's Bean, *Juniperus Communis*, Kachur, Kalmegh, Kamoteng Kahoy, Kanma, Kan-ts'ao, Kappa, Katphala, Kava Kava, Kelp, Kelpware, Kemangen, Keyflower, Key of Heaven, Khas Khas, Khat, Khella, Kiawe, Kidney Stone Tree, King Of Bitters, King's-clover, King's Crown, King's Cure, King's-cure-all, Kinnikinnick, Kiryat, Klamath Weed, Knitback, Knitbone, Knotgrass, Knotted Kelp, Knotted Marjoram, Knotted Wrack, Knotty Brake, Knotweed, Kola Nut, Korean *Ginseng*, Kua-lou, Kuawa, Kudzu, Kuei, Kumari, Kumaru, Kuo-lao, K'u-tou, Ku Ts'ai, Lactucarium, *Lactuca Virosa*, Ladder-to-heaven, Ladies'-delight, Ladies' Seal, Lady Bleeding, Lady's Bedstraw, Lady's Slipper, Lady's Mantle, Lady's-washbowl, Lai-ei-ts'ao, Lamb Mint, *Lamium Album*, Lammint, Lang-tu, Langue de Boeuf, Lapacho, *Lappa, Lappa* Minor, Large Fennel, Large-leaved Germander, Larrea *Tridentata, Latherwort, Laurus Nobilis*, Lavender, Lavender Giant Hyssop, *Lavandula officinalis*, Lawn Chamomile, Lawsonia *inermis*, Leafcup, Lebanese Oregano, Leeks, Lemon, Lemon Balm, Lemon Thyme, Lemon *Verbena*, Lemongrass, Lentinus *Edodes, Leonurus Cardiaca*, Leopard's Bane, *Lepidium meyenii*, Leptandra, Leptandra *Virginica, Leptospermum scoparium*, Lesser Indian Cress, Lesser Periwinkle, Le-ts'ao, Lettuce Opium, *Levisticum Officinale*, Lian Qiao, Licorice, Licorice Mint, Licorice Root, Life Root, Lignum Vitae, *Ligusticum Porteri, Ligustrum Vulgare*, Lily Convalle, Lily of the Valley, Limaosinho, Limeblossom, Lime Flowers, Lime Mint, Lime Tree, Linden, Linden Flower, *Lindera benzoin*, Ling Chi, Ling-t'ung, Ling Zhi, Link, Linseed, Lint Bells, *Linum Usitatissimum*, Lion's Ear, Lion's Foot, Lion's Tail, Lion's Tart, Lion's Tooth, Lippia *graveolens*, Lipstick Tree, Liquorice, Live-Forever, Live-Long, Liver Lily, Liverwort, Lizard's Tail, *Lobelia, Lobelia Inflata*, Longevity Herb, *Lonicera* Caprifolium, *Lonicera Japonica, Lonicera* Spp, Loodroot, Loosestrife, Lophophora williamsii, *Lotus, Lotus Corniculatus*, Lousewort, Lovage, Love Apples, Love in Winter, Love-lies-bleeding, Love Persley, Love Vine, Lucerne, Lu Hui, Lungwort, Luole, Lychee, Litchi *chinensis, Lycium, Lycium Chinese, Lycium* Fruit, Lycopodium, Lycopodium *clavatum, Lycopus americanus, Lysimachia christinae, Lysimachia vulgaris, Lythrum salicaria*, Ma Bian Cao, Macadamia Nut, Macadamia spp., Maca, Maca-Maca, Mace, Macochihua, Madagascar Periwinkle, Mad Apple, Madder, Madder Root, Madderwort, Mad Dog, Madweed, Madrone Tree, Ma huang, Maidenhair Fern, Maidenhair Tree, Maid's-hair, Maino, Maitake, Maize, Maka, Malabar Cardamom, Malabar Plum, Malabar Tamarind, Mal-dos-sete-dias, Male Fern, Mallow, *Malpighia* species, *Malus communis, Malva sylvestris*, Mamey Sapote, Manac, Mandioc, *Mandragora, Mandragora officinarum*, Mandrake, Mangosteen Oil Tree, *Manihot esculenta*, Manioc, Manioc Root, Manna Grass, Man-t'ien-hsing, Manuka, Manuka Myrtle, Manuka Tree, Manzanilla, Maqui, Maramar, Maranta Arundinaceae, Maranta Starch, Marapuama, Mare's Tail, Marigold, Maroochi Nut, *Marrubium, Marrubium Vulgare*, Marshmallow, Marsh Marigold, Marsh Parsley, Marsh Trefoil, Marsh Woundwort, *Marum*, Marvel, Mary Bud, Mary Golde, Mary Gowles, Mary Jane, Maryland Pink, Mary's Grass, Mary's Mantle, Mary's Thistle, Master of the Woods, Masterwort, Mastic, Mate, *Matricaria Chamomilla*, May, Mayapple, May Blossom, Maybush, May Lily, Maypop, *Maytenus, Maytenus* Species, May Tree, Meadow Clover, Meadow Eyebright, Meadow Saffron, Meadow Sage, Meadowsweet, Mealberry, *Medicago Sativa*, Mei-ts'ao, *Melaleuca, Melaleuca* Alternifolia, Melegueta Pepper, Melilot, Melilotus *officinalis, Melissa, Melissa officinalis*, Melmot Berry, *Mentha* haplocalyx, *Mentha piperita, Mentha pulegium, Mentha requienii, Mentha suaveolens, Mentha spicata*, Menthol Mint, *Mentha* x *piperita citrata*, Menyanthes *Trifoliata, Mercurialis Perennis*, Mescal, Meshasringi, Mesquite, Methi, Mexican Mint, Mexican Oregano, Mexican Poppy, Mexican Potato, Mexican Tea, Mexican Thyme, Mexican Wild Yam, Mexico Seed, Middle Comfrey, Mignonette Tree, Mi-kan, Milfoil, Milk Ipecac, Milk Thistle, Milkwort, Millefoil, Mint, Mints, Miracle Herb, Miracle Tea, Mistletoe, *Mitchella Repens*, Mi-tieh-hsiang, Mi-ts'ao, Moccasin Flower, Mogo, Molina, Mo Li Hua, *Momordica Charantia*, Monarda Didyma, Monkey-Bread Tree, Monkshood, Monk's Pepper, Moonflower, Moon Grass, Moose Elm, *Morinda, Morinda citrifolia, Morinda officinalis*, Mormon Tea, Moroccan Ironwood, Mortification Root, Moms nigra, Mother-of-thyme, Mother's-heart, Motherwort, Moujean Tea, Mountain *Arnica*, Mountain Ash, Mountain Aspen, Mountain Balm, Mountain Berry, Mountain Box, Mountain Cranberry, Mountain Daisy, Mountain Grape, Mountain Holly, Mountain Mint, Mountain Savory, Mountain Strawberry, Mountain Tobacco, Mountain Tea, Mouse-ear, Mugwort, Muira Puama, Mujonso, Mulberry, Mullein, Murraya koenigii, Muscatel Sage, Mu-Su, Mu Tong, Mu-yao, Myrciaria *dubia, Myrica, Myrica* Cerifera, Myricae Cortex, *Myristica Fragrans*, Myroxylon Balsamum, Myroxylon *Pereirae*, Myrrh, Myrrhis *odorata*, Myrtle, Myrtle Pepper, *Myrtus communis*, Nagara, Naidi, Naked Ladies, Napa Cabbage, Nappa, Narrow Dock, Narthex, Nashia *inaguensis*, Nasturtium *Officinale*, Naughty Man's Cherries, Neem, *Nelumbo nucifera*, Nenuphar, Nep, *Nepeta Cataria*, Nerveroot, Nettle, Nettle Flowers, New England Pine, New Jersey Tea, New Zealand Tea Tree, Niando, *Nicotiana Rustica*, Nightshade, Night Willow Herb, Nine Hooks, Nine Joints, Nip, Nira, Niu Bang, Noble Chamomile, Noble Yarrow, Nodding Wakerobin, Noni, Normandy Cress, Northern Pine, Northern Spicebush, Northern White Cedar, Norwegian Kelp, Nosebleed, Nutmeg, Nux Vomica, *Nymphaea Alba*, Oak, Oats, *Ocimum basilicum, Ocimum tenuiflorum, Oenothera Biennis*, Ohio *Curcuma*, Oil plant, Oilnut, Oil Nut Tree, Old English Lovage, Old-maid's-nightcap, Old-maid's-pink, Old Man, Old-man's-beard, Old Man's Nightcap, Old Man's Pepper, Old woman, *Olea Europaea*, Olibanum, Olive, Omam, Omum, One-berry, Onion, Opium Poppy, *Oplopanax hor-* ridus, Orange, Orange Mint, Orange Root, Ordeal Bean, Oregano, Oregano Brujo, Oregon Grape, Oriental Garlic, Oriental Mustard, Oriental Poppy, *Origanum majorana, Origanum syriacum, Origanum vulgare*, Orpine, Orris Root, Osha, Osterick, Oswego Tea, Our-Lady's-bedstraw, Our-Lady's-tears, Oval Buchu, Owler, Oxadoddy, Ox Balm, Ox Heart, Ox-tongue, Pacific Madrone, Pacific Yew, Padmaka, *Paeonia officinalis*, Paico, Paigle, Palisade Pine, Palma Christi, Palmaria *Palmata*, Palmetto, *Panax Ginseng, Panax* Quinquefolium, Panay, Pansy, *Papaver orientale, Papaver Rhoeas, Papaver Somniferum, Papaya*, Paper Birch, Papoose Root, Paracress, Paraguay Tea, *Pareira, Parell, Parietaria officinalis*, Pariswort, Parsley, Parsnip, Partridgeberry, Pasque Flower, *Passiflora, Passiflora Incarnata*, Passion Flower, Passions, Passion Vine, *Pastinaca sativa*, Patchouli, Patience Dock, Patience Herb, Pau d'Arco, Paullinia Cupana, Pausinystalia Yohimbe, Pauson, Peepal Tree, Pei-ma, Peking Cabbage, *Pelargonium, Pelargonium* sidoides, *Pelargonium* species, Pellitory, Pellitory Of The Wall, Pembina, Pennyroyal, Peony, Pepperidge Bush, Peppermint, Pepperweed, Perfume Tree, Periploca Of The Woods, *Persea Americana*, Persian Berries, *Persicaria odorata, Personata*, Peruvian Balsam, Peruvian Bark, Peruvian Ginseng, Peruvian Ground Cherry, *Petasites hybridus*, Petokal, Petroselinum Crispum, Peumus Boldus, Peyote, Pfaffia *paniculata*, Philanthropos, Phudina, Phyllanthus, Phyllanthus emblica, Phyllanthus niruri, *Physalis* Alkekengi, *Physalis peruviana* L., Physic Root, *Physostigma venenosum, Phytolacca americana, Picrasma excelsa*, Pigeon's Grass, Pignoli, Pigweed, Pikake, Pill-Bearing Spurge, Pilocarpus Microphyllus, Pilosella, Pimbina, *Pimenta Dioica, Pimenta officinalis*, Pimpinella Anisum, Pine, Pine Nut, Pineapple, Pineapple Strawberry, Pineapple *Verbena*, Pinkroot, Pink Rose, Pinon Nut, *Pinus* spp., *Pinus Strobus, Pinus Sylvestris*, Pinyon Pinenut, *Piper* betle, *Piper cubeba, Piper Methysticum, Piper Nigrum*, Pipe Tree, Pipsissewa, Pistachio, *Pistacia vera*, Piscidia piscipula, Pissabed, Pistachio, *Plantago Major, Plantago Psyllium, Plantago* Seed, Plantain, *Plectranthus amboinicus*, Pleurisy Root, Plum Rose, *Podophyllum peltatum*, Poet's *Jasmine*, Pogostemon cablin, Poha Berry, Poison Ash, Poison Flag, Poison Parsley, Poison Tobacco, Pokeroot, Pokeweed, Polar Plant, Polygala Senega, *Polygonatum Multiflorum, Polygonum* Aviculare, *Polygonum bistorta, Polygonum multiflorum, Polygonum odoratum, Polypodium vulgare*, Polypody, Poor Man's Ginseng, Poor-man's-treacle, Poplar, Popotillo, *Populus alba, Populus Tremuloides, Poria, Poria cocos, Portulaca Oleracea*, Pot, Potato Bean, Potency Wood, *Potentilla anserina, Potentilla erecta, Potentilla reptans*, Potenzholz, Pot Marigold, Pouteria sapota, Pouteria campechiana, Prairie Smoke, Prickly Ash, Prickly Lettuce, Prickly Pear Cactus, Prickly Poppy, Priest's-crown, Prim, Primrose, *Primula* Veris, Prince's Feather, Prince's-pine, Privet, *Prosopis pallida* syn. *Prosopis limensis*, Provence Rose, Prunella, Prunella vulgaris, *Prunus* Amygdalus, *Prunus Dulcis, Prunus Serotina, Prunus Spinosa, Psidium Guajava*, Psoralea, Psoralea corylifolia, Psoralea Fruit, *Psyllium, Ptychopetalum ovata, Pueraria Lobata*, Puff Ball, Pu gong ying, Pukeweed, Pukung-ying, *Pulmonaria officinalis, Pulsatilla*, Pumpkin, Pumpkin Pine, Puncture Vine, Purging Buckthorn, Purple *Angelica*, Purple Betony, Purple Clover, Purple Coneflower, Purple Foxglove, Purple Leptandra, Purple Loosestrife, Purple Medic, Purple Passionflower, Purple Rocket, Purplestem *Angelica*, Purslane, Pygeum, Pygeum *Africanum*, Pyrethrum, Pyrola *Umbellata*, Quack Grass, Quaking Aspen, Quassia, Quassia Bark, Quassia Wood, Quebra Pedra, Queen Annes Lace, Queen Of The Meadow, Queensland Nut, Queen's Delight, Queen's-root, *Quercus alba*, Queue de Lezard, Quickbeam, Quick-set, Quince, Quinine Tree, Quinsy Berries, Quiverleaf, Race Ginger, Racoon Berry, Rainbowweed, Rashona, Raspberry, Raspberry Leaf, Rat's Tail, Rattlebush, Rattleroot, Rattlesnake Root, Rattleweed, Rau Ram, Rauwolfia, Rauwolfia *Serpentina*, Red Alder, Red Balm, Red Bearberry, Red-bearded, Red Bergamot, Redberry Tea, Red Bush Tea, Red Clover, Redcole, Red Dulse, Red Eyebright, Red Legs, Red Paint Root, Red Pollom, Red Poppy, Red Puccoon, Red Raspberry, Red Robin, Red Root, Red Root Sage, Red Rose, Red Sage, Red Sorrel, Red Sunflower, Red Tea, Red *Trillium*, Red-veined Dock, Reefer, Rehmannia, Rehmannia *Glutinosa*, Reishi, *Rhamnus Cathartica, Rhamnus* Frangula, *Rhamnus Purshiana*, Rheumatism Root, Rheumatism Weed, Rheum *Palmatum, Rhodiola, Rhodiola* sacra, Rhubarb, *Rhus trilobata, Ribes Nigrum*, Ribwort, Richweed, *Ricinus Communis*, Rimed *scutatus*, Ritha, *Robinia Pseudoacacia*, Rock Brake, Rock Fern, Rockweed, Roman Chamomile, Roman Cumin, Roman Fennel, Rooibos, Root Of The Holy Ghost, Roquette, *Rosa Canina, Rosa Centifolia, Rosa Gallica*, Rose, Rose Apple, Roselle, Rosemary, Rosemary Plant, Rose-noble, Rose Root, Rosin Rose, *Rosmarinus officinalis*, Rosy Periwinkle, Rou Dou Kou, Round Buchu, Round-leaved Dock, Round-leafed Mint, Round-leaved Sorrel, Rowan Tree, Royal Herb, Royal *Jasmine*, Rub Cherry, *Rubia tinctoria, Rubus* Fructicosus, *Rubus Idaeus*, Rucola, Rue, Rugula, Rumara, *Rumex Acetosella, Rumex Crispus, Rumex Hymenosepalus, Rumex Obtusifolius*, Running Club Moss, Ruscus *Aculeatus*, Russian Chamomile, Russian Mustard, Rustic's Treacle, *Ruta Graveolens, Sabal, Saccharum officinarum*, Sacred Bark, Sacred Basil, Sacred Fig, Sacred *Lotus*, Sacred Plant, Sacred Sage, Sacred Tree, Sacred Water *Lotus*, Safflower, Saffron, Sagackhomi, Sage, Sage-leaved Germander, Sage Of Bethlehem, Saké, Salad Burnet, Salad Chervil, Salad Rocket, Salai Gugal, *Salix Alba*, Saloip, *Salvia, Salvia* apiana, *Salvia hispanica, Salvia* Miltiorrhiza, *Salvia officinalis, Salvia Sclarea, Sambucus Nigra*, Sampson Root, Sandalwood, Sandberry, Sangre de Drago, Sangue de Drago, *Sanguinaria, Sanguinaria canadensis*, Sanguisorba Minor, Sanguisorba *officinalis*, Sanicle, Sanicula *Europaea*, Sanicula *Marilandica, Santalum* Album, Sapin, Sapindus mukorossi, *Saponaria officinalis*, Sapote, Sarapia, Sarepta Mustard, Sarothamnus *Scoparius*, Sarpagandha, Sarsaparilla, *Sassafras, Sassafras Albidum*, Satan's Apple, Satavar, Satinflower, *Satureja hortensis, Satureja montana*, Saventaro, Savory, Saw Palmetto, Saxifrax, Scabish, Scabwort, Scarlet Bergamot, Scarlet Monarda, Scarlet Sage, Scarweed, Scented Fern, Scented Sumac, Schisandra, Schisandra *Chinensis*, Schizonepeta, Schizonepeta *tenuifolia*, Scopolia, Scopolia carniolica, Scotch Broom, Scotch Fir, Scotch Heather, Scotch Pine, Scots Pine, Scouring Rush, Scrofula Plant, Scrophularia *Nodosa*, Scurfy Pea, Scurvy Grass, Scurvy Weed, Scutelaria *Baicalensis*, Scutellaria Lateriflora, Sea Buckthorn, Sea Lettuce Flakes, Sea Oak, Sea Onion, Sea Parsley, Seaweed, Seawrack, Sedum Telephium, Self-Heal, Seneca Snakeroot, *Senecio Aureus*, Seneca Grass, Senega, Senega Root, *Senna*, Sereh, Serenoa *Repens, Serpentary, Serpyllum*, Setwall, Shameface, Shan-cha, Sha-ren, Shan-yao, Shatamull, Shatapushpa, Shatavari, Shave Grass, Shea Tree, Sheepberry, Sheep Sorrel, Sheng Di, Sheng Di Huang, Sheng Ti Huang, Shen Jiang, Shepherd's Knot, Shepherd's Needle, Shepherd's Purse, Shi Chang Pu, Shield Fern, Shih-lo, Shihuahuaco, Shiitake, Shiny *Asparagus*, Shirokikurage, Shoofly, Short Buchu, Short-leaved Buchu, Shovelweed, Shu Di Huang, Shu Ti Huang, Siberian *Ginseng*, Sicklewort, Silkweed, Silver Birch, Silver Fir, Silver Leaf, Silver-leaf Poplar, Silver Mint, Silver Pine, Silver Poplar, Silver Tree-ear Fungus, Silverweed, *Silybum*, Silymarin, Simply Jack, *Sinapis alba*, Skullcap, Skunkbush, Skunkbush Sumac, Skunk Cabbage, Slippery Elm, Sloe, Smallage, Smallanthus sonchifolius, Small Nasturtium, Smelling-stick, *Smilax* Uti Lis, Smooth Cicely, Smooth Strophanthus, Snakebite, Snake Lily, Snake Root, Snakeweed, Snapping Hazelnut, Snap-Wood, Snowball Tree, Snowdrop Tree, Snowflake, Snowflower, Snow Fungus, Soap Berry, Soapnut, Soapwort, Soft Pine, *Solanum Dulcamara*, Soldier's Cap, Soldier's Woundwort, *Solidago canadensis*, Solidago Virgaurea, Solis Sponsa, Solomon's Seal, Solsequia, Son-before-the-father, *Sorbus Aucuparia*, Sour Dock, Sour Grass, Soursop, Sour Weed, Southern *Ginseng*, Southernwood, Sowberry, Soy, Soya, Soybean, Spanish Chamomile, Spanish Chestnut, Spanish *Jasmine*, Spanish Thyme, Spearmint, Speedwell, Spiceberry, Spicebush, Spicewood, Spicy Wintergreen, Spigelia *Marilandica*, Spike Lavender, Spiked Loosestrife, Spikenard, *Spilanthes acmella*, Spoonwood, Spoonwort, Spotted Alder, Spotted Thistle, Spring Cress, Spring Wintergreen, Square Stalk, Squawbush, Squaw Root, Squaw Tea, Squaw Vine, Squill, Stachys *officinalis*, Stachys *Palustris*, Stagbush, Staghorn, Stanchgrass, Star Anise, Starbloom, Star Flower, Star Fruit, Star Grass, Starweed, Starwort, *Stellaria, Stellaria Media*, Stickwort, St. Ignatius Bean, Stillingia *Sylvatica*, Stingnose, Stinking Benjamin, Stinking Christopher, Stinging Nettle, Stingless Nettle, Stinking Nightshade, Stinking Roger, Stinking Rose, Stinking Weed, Stinking Willie, Stinkweed, Stitchwort, St. John's Bread, St. John's Grass, St. John's Plant, St. John's Wort, St. Josephwort, Stonecrop, Stone Root, Strawberry, Stork's Bill, Strawberry Tomato, Strawberry Tree, Striped Alder, Strophanthus, Strophanthus Gratus, Strychnine, Strychnine Tree, Strychnos nux-vomica, *Styrax Benzoin*, Succory, Sudanese Tea, Sugar Cane, *Sui* Hoi, Suma, Su Nanesi, Sundew, Sunflower, Sunkfield, Sunthi, Surasa, Suterberry, Swallowwort, Swamp Cedar, Swamp Root, Sweating Plant, Sweet Almond, Sweet Balm, Sweet Basil, Sweet Bay, Sweet Birch, Sweet Bracken, Sweet Brake, Sweet Bugle, Sweet Cane, Sweet Chervil, Sweet Chestnut, Sweet Cicely, Sweet Clover, Sweet Coltsfoot, Sweet Cumin, Sweet Dock, Sweet Elm, Sweet Fennel, Sweet Fern, Sweet Flag, Sweet Flag Rhizome, Sweet Goldenrod, Sweet Grass, Sweet *Iris*, Sweet Lavender, Sweet Licorice, Sweet Lucerne, Sweet Marjoram, Sweet Myrrh, Sweet Root, Sweet Rush, Sweet-scented Geranium, Sweet Tea Vine, Sweet Tongue, Sweet Violet, Sweetweed, Sweet Wood, Sweet Woodruff, Swertia, Swertia chirayita, Swine Snout, Symphytum *Officinale*, Symplocarpus *Foetidus*, Syrian Oregano, Syzygium cumini, Syzygium jambos, *Tabebuia* Spp., Tagara, Taheebo, Ta-huang, Tailed Cubebs, Tailed Pepper, Tailwort, Tall Nasturtium, Tallow Shrub, Tall Speedwell, Tall *Veronica*, Tamanu Nut Tree, Tamarind, Tamarindus Indica, Tamus, *Tanacetum Parthenium, Tanacetum Vulgare*, Tang Kuei, Tanners Bark, Tanner's-dock, Tan Shen, Tansy, Tap *Aloe*, Tapioca-root, *Taraxacum Officinale*, Tarragon, Tartar Root, Tarweed, *Taxus Brevifolia*, Teaberry, Teasel, Tea Tree, *Te Limon*, Telltime, *Tenuifolia, Terminalia arjuna, Tetterberry, Tetterwort, Teucrium marum, Teucrium scorodonia, Thali, Theobroma Cacao*, Thorn Apple, Thorn Poppy, Thorntree, Thorny Burr, Thoroughwort, Thousand-leaf, Thousand-seal, Three-leaved Caper, Three-leaved Nightshade, Throatwort, *Thuja, Thuja Occidentalis*, Thumb, *Thunberg Fritillaria* Bulb, Thyme, *Thymus citriodorus, Thymus Serpyllum, Thymus vulgaris*, Tian Men Dong, Tibetan *Rhodiola*, T'ien-shih-li, Ti Huang, Ti Huang Chiu, *Tilia Americana, Tilia Cordata, Tilia europea*, Tipton Weed, Toad Flax, Tobacco Wood, Tokal, Tomillo, Tom Thumb Nasturtium, Tongue Grass, Tonka, Tonka Bean, Tonka Bean Tree, Tonquin Bean, Toothache Plant, Toothache Tree, *Trachyspermum ammi*, Treacle Mustard, Tree Moss, Tree of Joy, Tree of Life, Tree's Dandruff, Trefoil, Trembling Aspen, Trembling Poplar, *Tremella fuciformis, Tribulus, Tribulus terrestris*, Tricolor Garlic, *Trifolium pratense, Trifolium repens, Trigonella, Trigonella* Foenum-Graecum, *Trillium, Trillium erectum, Triticum aestivum, Tropaeolum minus*, Tormentil, True Angostura, True Chamomile, True Lavender, True Oregano, True Sage, True Taragon, True Unicorn Root, Tse-lan, Tuber Root, Tuckahoe, Tulasi, Tulsi, Tumeric Root, Tuna Cactus, Turkey Burrseed, Turkish Oregano, Turmeric, *Turnera diffusa*, Turtlebloom, Turtlehead, *Tussilago farfara*, Twak, Twinflower, Tzu-mo-lo, Uassi, *Ulmus rubra*, Uma, Umbrella Plant, Umcka, Umckaloabo, Una De Gato, *Uncaria tomentosa, Undaria pinnatifida*, Upland Cotton, Upland Cress, Upland Cranberry, Uppagi, Upside-Down Tree, *Urginea maritima, Urtica dioica, Usnea, Usnea* spp., *Uva ursi, Vaccinium macrocarpon, Vaccinium myrtillus, Valerian, Valeriana officinalis*, Vandalroot, *Vanilla, Vanilla fragrans, Vanilla* Grass, *Vanilla planifolia, Varuna*, Vegetable Antimony, Vegetable Marrow, Vegetable Sulfur, Vegetable Tallow, Vegetable Wax, Venus' Basin, Venus'-hair Fern, *Verbascum thapsus, Verbena, Verbena officinalis*, Vermont *Valerian, Vernonia amygdalina, Veronica beccabunga, Veronica officinalis*, Vervain, Vetiver, *Vetiveria zizanioides*, Vetivert, *Viburnum opulus, Viburnum prunifolium*, Vietnamese Cilantro, Vietnamese Coriander, Vietnamese Mint, *Vinca minor, Vinca rosea*, Vine, *Viola odorata, Viola* Tricolor, Violet-bloom, Virginia Bugleweed, Virginia Dogwood, Virginia Prune, Virginia Skullcap, Virginia Snakeroot, Virginia Water Horehound, *Viscum album, Visnaga, Vitellaria paradoxa, Vitex, Vitex Agnus-Castus, Vitis vinifera*, Vomitroot, Wachsgagl, Wakame, Wake Robin, Waldmeister, Wallflower, Walnut, Wasabi, *Wasabia japonica*, Wasei, Water Bugle, Watercress, Water Dragon, Water Flag, Water Horehound, Water Hyssop, Water Lily, Water Mint, Water Pimpernel, Water Shamrock, Water Thistle, Wattle, Wax Cluster, Wax Dolls, Wax Myrtle, Way Bennet, Weeping Ash, Weeping Forsythia, Wheatgrass, Whinberry, Whippoorwill's-shoe, Whistling Thorn, White Archangel, White Ash, White Birch, White Bird's-eye, White Bryony, White Cedar, White Ceremonial Sage, White Chamomile, White Clover, White Deadnettle, White Endive, White Flower De Luce, White Horehound, White Jelly-leaf, White Muer, White *Lotus*, White Mustard, White Nettle, White Pine, White Poplar, White Sage, White Tansy, Whitethorn, White Tree-ear, White Turmeric, White Walnut, White Willow, Whitten Tree, Whorlywort, Whortleberry, Whorts, Wild Allspice, Wild *Angelica*, Wild Black Cherry, Wild Brier, Wild Bryony, Wild Carrot, Wild Celery, Wild Chamomile, Wild Chicory, Wild Cotton, Wild *Crocus*, Wild Endive, Wild Fennel, Wild Geranium, Wild Hops, Wild Indigo, Wild *Iris*, Wild Lemon, Wild Lettuce, Wild Mandrake, Wild Marjoram, Wild Oats, Wild Opium, Wild Pansy, Wild Parsnip, Wild Passionflower, Wild Pieplant, Wild Rhubarb, Wild Rye, Wild Snakeroot, Wild Strawberries, Wild Succory, Wild Sunflower, Wild Sweetsop, Wild Tansy, Wild Teasel, Wild Thyme, Wild Tobacco, Wild Valerian, Wild Vine, Wild Yam, Willow, Willow Herb, Windflower, Wind Root, Wineberry, Winter Berry, Winterbloom, Winter Cherry, Winter Clover, Wintergreen, Winterlien, Winter Marjoram, Winter Savory, Winter Thyme, Winterweed, Witches'-moneybags, Witchgrass, Witch Hazel, Witch's Bells, Withania, Withania Somnifera, Wolfsbane, Wolf s Claw, Woman's Long Hair, Wood Betony, Woodbine, Wood Boneset, Wood Ear Fungus, Woodland Germander, Woodland Strawberry, Wood Licorice, Woodruff, Wood Sage, Wood Strawberry, Wood Turmeric, Wood Vine, Woodward, Woody Nightshade, Woolly Mint, Woolly Thistle, Worm Grass, Wormseed, Wormweed, Wormwood, Woundwort, Wu-pa-ho, Wu-wei-zi, Wycopy, Xiao-hue-xiang, Xi Shu, Xu Ku Cao, Yacon, Yacuma, Yang-Mei, Yape, Yarrow, Yasmin, Yasti Madhu, Yawroot, Yellow Bedstraw, Yellow Cedar, Yellow Dock, Yellow Eye, Yellow *Ginseng*, Yellow Indian Paint, Yellow Indian Shoe, Yellow Indigo, Yellow *Jasmine*, Yellow Jessamine, Yellow Lark's Heels, Yellow Locust, Yellow Loosestrife, Yellow Melilot, Yellow Mustard, Yellow Paint Root, Yellow Poppy, Yellow Puccoon, Yellow Rocket, Yellowroot, Yellow Thistle, Yellow Vine, Yerba, Yerba Buena, Yerba Mansa, Yerba Manza, Yerba Santa, Yin-hsing, Yin Yang Huo, Ylang Ylang Tree, Yohimbe, Yohimbine, *Yucca, Yucca* spp., Yueh-kuei, Yuma, Yu Mi Shu, Yuzu, Yuyu Chonta, Zaatar, Zacate *Limon, Zanthoxylum Americanum, Zea Mays*, Zedoary, or *Zingiber Officinale*.

Probiotics can also be included in cannabinoid compositions prepared according to the invention. Examples of suitable probiotics include, but are not limited to, *Acinetobacter calcoaceticus, Arthrobacter agilis, Arthrobacter citreus, Arthrobacter globiformis, Arthrobacter luteus, Arthrobacter simplex, Azotobacter chroococcum, Azotobacter paspali, Azospirillum brasiliense, Azospirillum lipoferum, Bacillus* ssp. (e.g., *Bacillus brevis, Bacillus coagulans, Bacillus laterosporus, Bacillus marcerans, Bacillus pumilus, Bacillus polymyxa, Bacillus sphaericus, Bacillus subtilis*), *Bacteroides lipolyticum, Bacteroides succinogenes, Bifidobacterium* ssp. (e.g., *Bifidobacterium animalis lactis, Bifidobacterium bifidum, Bifidobacterium infantis, Bifidobacterium lactis, Bifidobacterium longum, Bifidobacterium animalis, Bifidobacterium breve*), *Brevibacterium lipolyticum, Brevibacterium stationis, Enterococcus faecium, Kurthia zopfii, Lactobacillus* ssp. (e.g., *Lactobacillus acidophilus, Lactobacillus brevis, Lactobacillus bulgaricus, Lactobacillus casei, Lactobacillus delbrueckii LE, Lactobacillus gasseri, Lactobacillus helveticus, Lactobacillus lacris, Lactobacillus paracasei, Lactobacillus plantaruntarum, Lactobacillus reuteri, Lactobacillus rhamnosus, Lactobacillus salivarius, Lactobacillus sporogenes*), *Myrothecium verrucaria, Pseudomonas calcis, Pseudomonas dentrificans, Pseudomonas fluorescens, Pseudomonas glathei, Phanerochaete chrysosporium, Saccharomyces boulardii, Saccharomyces cerevisiae, Streptococcus thermophilus, Streptomyces fradiae, Streptomyces cellulosae, Streptomyces griseoflavus*, and combinations thereof.

Homeopathic remedies can also be included in cannabinoid compositions prepared according to the invention. Examples of suitable homeopathic remedies and indications that can be treated with homeopathic remedies include, but are not limited to, adrenocorticotropic hormone (ATCH), *Abies canadensis, Abies nigra, Abrotanum, Absinthium, Acacia Arabica, Acalypha Indica*, Acetaldehyde, Acetanilidum, *Aceticum acidum*, Acetylsalicylicum acidum, *Achyranthis calea*, Aconite or *Aconitum Nap, Aconitum ferox, Aconitum lycoctonum, Aconitum napellus, Aconitum, Radix, Acorns calamus* or *Calamus, Actaea Spicata* Acrylate, *Actaea* Rac or *Cimicifuga, Actaea spic, Adamas, Adelheidsquelle, Adenosinum Cyclophosphoricum, Adeps Suillus*, Adipose Tissue, *Adonis Vernalis*, Adrenal Cortex, Adrenal Gland, Adrenalinum or Epinephrine, Adrenocorticotrophin, *Aesculinum, Aesculus Carnea, Flos, Aesculus Glabra, Aesculus Hippocastanum, Aesculus Hippocastanum Flos, Aethiops Antimonialis, Aethiops Mercurialis-Mineralis, Aethusa Cynapium, Agaricinum, Agaricus campanulatus, Agaricus Campestris, Agaricus Citrinus, Agaricus emeticus, Agaricus muscarius, Agaricus pantherinus, Agaricus phalloides, Agaricus procerus, Agaricus semiglobatus, Agaricus stercorarius, Agave americana, Agave tequilana, Agnus castus, Agraphis nutans, Agrimonia eupatoria, Agrimonia eupatoria, Flos, Agrimonia odorata, Flos, Agrostemma githago, Ailanthus glandulosus, Aletris farinosa, Alfalfa, Alisma plantago, Allium Cepa, Allium sativum, Alloxanum, Alnus glutinosa, Alnus serrulata, Aloe socotrina, Alstonia constricta, Alstonia scholaris, Althaea officinalis*, Alumen or Alum, Alumina, Alumina *Silicata*, Aluminum *Metallicum*, Aluminum Muriaticum, *Ambra grisea, Ambrosia artemisiaefolia, Ammi visnaga, Ammoniacum gummi, Ammonium Aceticum*, Ammonium Benzoicum, Ammonium Bromatum, Ammonium Carbonicum, Ammonium Causticum, Ammonium Citricum, Ammonium Iodatum, Ammonium Muriaticum, Ammonium Nitricum, Ammonium Phosphoricum, Ammonium Picricum, Ammonium *Tartaricum*, Ammonium *Valerianicum*, Ammonium *Vanadium, Amorphophallus Rivieri, Ampelopsis quinquefolia, Amygdala amara, Amygdalae amarae* Aqua, *Amygdalae amarae oleum, Amygdalus persica, Amyl nitrosum, Anacardium occidentale, Anacardium orientate, Anagallis arvensis, Ananassa, Anas Barbariae Hepatis Et Cordis Extractum, Anatherum muricatum, Anchusa officinalis, Anemone nemorosa, Anemopsis californica, Anethum graveolens, Angelica archangelica, Angelica atropurpurea, Angelica sinensis, Radix, Angophora Lanceolata, Angustura vera, Anhalonium lewinii, Anilinum, Anilinum Sulphuricum, Anisum, Anthemis nobilis, Anthemis pyrethrum, Anthoxanthum odoratum, Anthracinum* (anthrax), Antimonium Arsenicicum, Antimonium *Crudum*, Antimonium Iodatum, Antimonium Muriaticum, Antimonium Oxydatum, Antimonium Sulphuratum *Aureum*, Antimonium *Tartaricum*, Antipyrinum, Apatite, Apiolum, *Apis mellifica, Apis venenum purum, Apium graveolens, Apocynum androsaemifolium, Apocynum cannabinum, Apomorphinum, Apomorphinum muriaticum*, Aqua *Marina, Aquilegia vulgaris, Aralia hispida, Aralia quinquefolia, Aralia racemosa, Aranea diadema, Arbutinum, Arbutus Andrachne, Areca catechu, Argemone mexicana, Argentum cyanatum, Argentum iodatum, Argentum metallicum, Argentum muriaticum, Argentum nitricum, Argentum oxydatum, Argentum phosphoricum, Aristolochia clematitis, Aristolochia milhomens, Aristolochia serpentaria, Arnica montana, Arnica montana, Radix*, Arsenicum *Album*, Arsenicum Bromatum, Arsenicum Iodatum, Arsenicum *Metallicum*, Arsenicum *Sulphuratum Flavum*, Arsenicum *Sulphuratum Rubrum, Artemisia vulgaris, Arum dracontium, Arum italicum, Arum maculatum, Arum triphyllum, Arundo mauritanica, Asafoetida, Asarum canadense, Asarum europaeum, Asclepias curassavica, Asclepias incarnata, Asclepias syriaca, Asclepias tuberosa, Asclepias vincetoxicum, Asclepias vincetoxicum folia, Asimina triloba, Asparagus officinalis, Asperula odorata, Astacus fluviatilis, Asterias Rubens, Astragalus menziesii, Atropinum, Atropinum sulphuricum, Aurum bromatum, Aurum iodatum, Aurum met, Arum mur, Aurum muriaticum kalinatum, Aurum muriaticum natronatum, Aurum sulphuratum, Avena sativa, Aviaire, Azadirachta indica*, Bacillinum of Burnet, Badiaga, Baja, Balsamum Peru, *Baptisia tinctoria, Barosma cren, Baryta Acetica*, Baryta *Carbonica*, Baryta *Iodata*, Baryta *Muriatica*, BCG, Belladonna, Belladonna, *Radix, Bellis Perennis*, Benzinum, Benzinum Dinitricum, Benzoicum *acidum, Benzoicum*, Berberinum, *Berberis Aquifolium, Berberis vulgaris, Berberis vulgaris, Fructus*, Beryllium *Metallicum, Beta vulgaris*, Betainum Muriaticum, *Betula Pendula*, Cortex, *Betula Pendula, Folia,*

Bismuthum *Metallicum*, Bismuthum *Oxydatum*, Bismuthum Subnitricum, *Bixa* Oreliana, *Blatta americana, Blatta orientalis*, Boldo, *Boletus luridus, Boletus satanas, Bombyx processionea, Borago officinalis, Borax*, Boricum *acidum, Botulinum, Bovista, Brassica napus*, Bromelain, Bromium, *Bromus ramosus, Flos*, Brucinum, *Bryonia alba, Bufo rana, Bunias orientalis, Buthus australis, Butyricum acidum, Buxus sempervirens, Cacao, Cactus grandiflorus, Cadmium bromatum, Cadmium iodatum, Cadmium metallicum, Cadmium muriaticum, Cadmium sulphuratum, Cadmium sulphuricum*, Caffeinum, Cahinca, Cajuputum, *Caladium seguinum, Calcarea acetica, Calcarea arsenicica, Calcarea sarbonica, Calcarea caustica, Calcarea fluorica, Calcarea hypochlorata, Calcarea hypophosphorosa, Calcarea iodata, Calcarea lactica, Calcarea muriatica, Calcarea oxalica, Calcarea phosphorica, Calcarea picrata, Calcarea silicata, Calcarea sulphurica, Calendula officinalis, Calluna vulgaris, Flos, Calotropis gigantea, Caltha palustris, Camphora, Camphora monobromata, Camphoricum acidum, Canchalagua, Candida albicans, Candida parapsilosis*, Canine Dapp, Cantharidinum, *Cantharis, Capsicum, Capsicum annuum, Carbo animalis, Carbo vegetabilis, Carbolicum acidum, Carboneum, Carboneum chloratum, Carboneum hydrogenisatum, Carboneum oxygenisatum, Carboneum sulphuratum, Carcinosinum, Cardiospermum, Carduus benedictus, Carduus marianus, Carpinus betulus, Flos, Cartilago suis, Carum carvi, Cascarilla, Cassada, Castanea sativa, Flos, Castanea vesca, Castor equi, Castoreum, Catalpa bignonioides, Caulophyllum thalictroides*, Causticum, *Ceanothus americanus*, Cedron, *Celtis occidentalis, Cenchris contortrix, Centaurea tagana, Centaurium umbellatum, Flos, Cephalanthus occidentalis, Cerasus virginiana, Ceratostigma willmottianum, Flos, Cereus bonplandii, Cereus serpentinus, Cerium oxalicum, Cetraria islandica*, Chamomilla, *Cheiranthus cheiri, Chelidonium majus, Chelidonium majus, Radix, Chelone glabra, Chenopodii glauci Aphis, Chenopodium anthelminticum, Chenopodium vulvaria, Chimaphila maculata, Chimaphila umbellata, Chininum arsenicicum, Chininum arsenicosum, Chininum muriaticum, Chininum purum, Chininum salicylicum, Chininum sulphuricum, Chionanthus virginica*, Chloralum, Chloramphenicolum, Chlorinum, Chloroforum, Chlorpromazinum, Cholera, Cholesterinum, Cholinum, Chromicum *acidum*, Chromium *Kali sulphuricum*, Chromium *Oxydatum*, Chromium *Sulphuricum, Chrysanthemum leucanthemum*, Chrysarobinum, *Cicer arietinum, Cichorium intybus, Cichorium intybus, Flos, Cicuta maculata, Cicuta virosa, Cimex lectularius, Cimicifuga racemosa, Cina, Cinchona officinalis, Cinchonium sulphuricum, Cineraria maritima, Cineraria maritima, Succus, Cinnamomum, Cistus canadensis*, Citricum *acidum, Citrus decumana, Citrus limonum, Citrus vulgaris, Clematis erecta, Clematis virginiana, Clematis vitalba, Flos, Clematis vitalba, Folia, Cobaltum Metallicum*, Cobaltum Muriaticum, Cobaltum Nitricum, *Coccinella septempunctata, Cocculus indicus, Coccus cacti, Cochlearia armoracia, Cochlearia officinalis*, Coenzyme A, *Coffea cruda, Coffea tosta*, Colchicinum, *Colchicum autumnale*, Colibacillinum, *Collinsonia canadensis*, Colocynthinum, *Colocynthis*, Colostrum, *Comocladia dentata*, Conchiolinum, Condurango, Coniinum, Coniinum Bromatum, *Conium maculatum, Convallaria majalis, Convolvulus arvensis, Copaiva officinalis*, Corailium *Rubrum, Corallorhiza odontorhiza, Coriaria ruscifolia, Cornus alternifolia, Cornus circinata, Cornus florida*, Cortisone *Aceticum, Corydalis canadensis, Cotyledon umbilicus*, Coumarinum, *Crataegus oxyacantha*, Cresolum, *Crocus sativus, Crotalus cascavella, Crotalus horridus, Croton tiglium*, Crotonchloralum, *Cubeba officinalis, Cucurbita citrullus, Cucurbita pepo. Flos, Cucurbita pepo, Semen, Culex musca, Cuphea petiolata, Cupressus australis, Cupressus lawsoniana*, Cuprum *aceticum*, Cuprum Ammonio-*Sulphuricum*, Cuprum Arsenicosum, Cuprum *Carbonicum*, Cuprum *Metallicum*, Cuprum Muriaticum, Cuprum Nitricum, Cuprum *Oxydatum Nigrum*, Cuprum *Sulphuricum*, Curare, *Cyclamen europaeum, Cydonia vulgaris, Cynara scolymus, Cynodon dactylon, Cypripedium pubescens*, Cysteinum, *Cytisus scoparius*, Damiana, *Daphne indica, Datura arborea, Datura metel*, DDT, Delphininum, *Derris pinnata, Dichapetalum, Dictamnus albus*, Digitalinum, *Digitalis purpurea*, Digitoxinum, *Dioscorea villosa*, Dioscoreinum, Diphtherinum, Diphtherotozinum, Diptherinum, Diptherotoxinum, *Dirca palustris*, DNA, *Dolichos pruriens, Doryphora decemlineata, Draba verna, Drosera rotundifolia*, DTTAB (Diptheria), *Duboisia myoporoides, Dulcamara, Dulcamara, Flos*, Dysentery, *E. Coli*, Ear, Labyrinth of (inner ear), Ear, Middle, Eberthinum, *Echinacea angustifolia, Echinacea purpurea, Elaeis guineensis, Elaps corallinus, Elaterium, Embryo suis, Emetinum, Enterotoccinum, Eosinum natrum, Ephedra vulgaris, Epigaea repens, Epilobium palustre, Epiphegus virginiana, Equisetum arvense, Equisetum hyemale, Eranthis hyemalis, Erechtites hieracifolia, Erigeron canadensis, Eriodictyon californicum, Erodium, Eryngium aquaticum, Eryngium maritimum, Erythraea centaurium, Eschscholtzia californica*, Eserinum, Etherum, Ethylicum, Ethylum Nitricum, Eucalyptol, *Eucalyptus globulus, Eugenia caryophyllata, Eugenia jambosa, Euonymus atropurpureus, Euonymus europaeus, Eupatorium aromaticum, Eupatorium cannabinum, Eupatorium perfoliatum, Eupatorium purpureum, Euphorbia amygdaloides, Euphorbia corollata, Euphorbia cyparissias, Euphorbia hypericifolia, Euphorbia lathyris, Euphorbia pilulifera, Euphorbium officinarum, Euphrasia officinalis*, Eupion, Eyebright herb, *Fagopyrum esculentum, Fagus sylvatica, Fagus sylvatica, Flos, Fel tauri*, Ferrum *Aceticum*, Ferrum Arsenicicum, Ferrum Bromatum, Ferrum *Carbonicum*, Ferrum Citricum, Ferrum Cyanatum, Ferrum Iodatum, Ferrum *Lacticum*, Ferrum *Metallicum*, Ferrum Muriaticum, Ferrum Pernitricum, Ferrum Phosphoricum, Ferrum Picricum, Ferrum *Sulphuricum*, Ferrum *Tartaricum*, Ferula *Glauca, Ficus Religiosa, Filix mas, Foeniculum vulgare*, Folliculinum, Formalinum, *Formica rufa*, Formicum *acidum, Fragaria vesca, Franciscea uniflora, Fraxinus americana, Fraxinus excelsior*, Fuchsinum, *Fucus vesiculosus, Fumaria officinalis, Fumaricum acidum, Funiculus umbilicalis suis, Galanthus nivalis, Galega officinalis, Galium aparine, Gallicum acidum, Galphimia Glauca, Gambogia*, Garlic, *Gaultheria procumbens, Gelsemium sempervirens, Genista tinctoria, Gentiana cruciata, Gentiana lutea, Gentiana quinqueflora, Gentianella amarella, Flos, Geranium maculatum, Geranium robertianum, Geum rivale, Geum urbanum, Ginkgo biloba, Glandula suprarenalis suis, Glechoma hederacea*, Glonoinum, Glycerinum, Glycogenum, *Glycyrrhiza glabra, Gnaphalium leontopodium, Gnaphalium polycephalum, Gnaphalium uliginosum*, Gonotoxinum, *Gossypium herbaceum*, Granatum, *Graphites, Gratiola officinalis*, Grindelia, Guaco, Guaiacum, *Guarea trichilioides, Guatteria gaumeri*, Gunpowder, *Gymnocladus canadensis, Haematoxylon campechianum, Haemophilus* Infl. B, Hair Bulb, Pilo Sebaceous Zone, *Hamamelis virginiana, Haronga madagas-cariensis, Hedeoma pulegioides, Hedera helix*, Hekla lava, *Helianthemum nummularium, Flos, Helianthus annuus, Heliotropium peruvianum, Helix tosta, Helleborus foetidus, Helleborus niger, Helleborus viridis, Heloderma, Helonias dioica, Hepar suis*,

*Hepar sulphuris calcareum, Hepar sulphuris Kalinum, Hepatica triloba,* Hepatitis A, Hepatitis B, Hepatitis C, *Heracleum sphondylium, Herpes zoster, Hippozaeninum, Hippuricum acidum, Hirudinum, Histaminum Hydrochloricum,* Hoang-Nan, *Hoitzia coccinea, Holarrhena antidysenterica, Homarus, Hottonia palustris, Flos, Humulus lupulus, Hura brasiliensis, Hura crepitans, Hydrangea arborescens, Hydrastininum muriaticum, Hydrastis canadensis, Hydrocotyle asiatica, Hydrocyanicum acidum, Hydrofluoricum acidum, Hydrophis cyanocinctus, Hydrophyllum virginianum, Hyoscyaminum, Hyoscyaminum, Hydrobromatum, Hyoscyamus niger, Hypericum perforatum, Hypothalamus, Iberis amara, Ichthyolum, Ignatia amara, Ilex aquifolium, Ilex aquifolium, Flos, Ilex paraguariensis, Illicium anisatum, Impatiens glandulifera, Flos, Imperatoria ostruthium,* Indigo, *Indium metallicum, Indolum, Influenzinum, Inula helenium, Iodium, Iodoformum, Ipecacuanha, Ipomoea stans, Iridium metallicum, Iris florentina, Iris foetidissima, Iris germanica, Iris tenax, Iris versicolor, Jacaranda caroba, Jalapa, Jasminum officinale, Jasper, Jatropha curcas, Jatropha urens,* Jequirity, *Jonesia asoca, Juglans cinerea, Juglans regia, Juglans regia, Flos, Juncus effusus, Juniperus communis, Juniperus virginiana, Justicia adhatoda, Kali aceticum, Kali arsenicosum, Kali bichromicum, Kali bromatum, Kali carbonicum, Kali causticum, Kali chloricum, Kali chromicum, Kali cyanatum, Kali ferrocyanatum, Kali iodatum, Kali muriaticum, Kali nitricum, Kali oxalicum, Kali permanganicum, Kali phosphoricum, Kali picricum, Kali silicatum, Kali sulphuricum, Kali tartaricum, Kali telluricum, Kalmia latifolia, Kamala, Karaka, Karwinskia humboldtiana, Kino australiensis, Kousso, Kreosotum, Laburnum anagyroides, Lac caninum, Lac defloratum, Lac felinum, Lac maternum, Lac vaccinum, Lacerta agilis, Lachesis mutus, Lachnanthes tinctoria, Lacticum acidum, Lactuca virosa, Lamium album, Lapis albus, Lappa major, Larix decidua, Flos, Lathyrus cicera, Lathyrus sativus, Latrodectus katipo, Latrodectus mactans, Laurocerasus,* Lecithin granules, Lecithin potenized, *Ledum palustre, Lemna minor, Leonurus cardiaca, Lepidium bonariense, Leptandra virginica, Lespedeza capitata,* Levico, *Levisticum officinale, Levomepromazinum, Liatris spicata, Lilium tigrinum, Limulus, Linaria vulgaris, Linum catharticum, Linum usitatissimum, Lithium benzoicum, Lithium bromatum, Lithium carbonicum, Lithium muriaticum, Lobelia cardinalis, Lobelia erinus, Lobelia inflata, Lobelia purpurescens, Lobelia syphilitica, Lobelinum, Lolium temulentum, Lonicera caprifolium, Flos, Lonicera periclymenum, Lonicera xylosteum, Lophophytum Leandri, Luesinum, Luffa operculata, Lupulinum, Lycopersicum esculentum, Lycopodium clavatum, Lycopus virginicus, Lysimachia nummularia, Lyssin, Lyssinum, Macrotinum, Magnesia carbonica, Magnesia muriatica, Magnesia oxydata, Magnesia phosphorica, Magnesia sulphurica, Magnesium metallicum, Magnolia glauca, Magnolia grandiflora,* Malaria off, *Malus pumila, Flos, Mancinella, Mandragora officinarum, Manganum aceticum, Manganum carbonicum, Manganum metallicum, Manganum muriaticum, Manganum oxydatum nativum, Manganum oxydatum nigrum, Manganum phosphoricum, Manganum sulphuricum, Mangifera indica, Marrubium vulgare,* Matico, *Matthiola graeca, Medorrhinum* (Gonorrheal virus), *Medulla ossis suis, Medusa, Melastoma ackermani, Melilotus alba, Melilotus officinalis, Melissa officinalis, Menispermum canadense, Mentha piperita, Mentha pulegium, Mentha viridis, Mentholum, Menyanthes trifoliata, Mephitis mephitica, Mercurialis perennis, Mercurius aceticus, Mercurius auratus, Mercurius bromatus, Mercurius corrosivus, Mercurius cum kali iodatus, Mercurius cyanatus, Mercurius dulcis, Mercurius iodatus flavus, Mercurius iodatus ruber, Mercurius methylenus, Mercurius nitricus, Mercurius praecipitatus albus, Mercurius praecipitatus ruber, Mercurius solubilis, Mercurius sulphocyanatus, Mercurius sulphuratus ruber, Mercurius sulphuricus, Mercurius vivus,* Methylene blue, *Mezereum, Millefolium, Mimosa pudica, Mimulus guttatus, Flos, Mitchella repens, Momordica balsamina, Mononucleosis, Monotropa uniflora, Morbillinum* (Measles), *Moschus, Mucosa nasalis suis,* Mullein essence, *Murex purpurea, Muriaticum acidum, Musa sapientum, Mygale, Myosotis arvensis, Myrica cerifera, Myristica sebifera, Myrrha, Myrtus communis, Nabalus serpentarius, Nadidum, Naja tripudians, Naphthalinum, Narceinum, Narcissus, Pseudo-, Narcissus, Narcotinum, Nasturtium aquaticum, Natrum arsenicicum, Natrum bicarbonicum, Natrum bromatum, Natrum carbonicum, Natrum fluoratum, Natrum hypochlorosum, Natrum lacticum, Natrum muriaticum, Natrum nitricum, Natrum nitrosum, Natrum oxalaceticum, Natrum phosphoricum, Natrum pyruvicum, Natrum salicylicum, Natrum silicofluoricum, Natrum sulphuratum, Natrum sulphuricum, Natrum sulphurosum,* Negundo, *Nepenthes, Nepeta cataria, Niccolum carbonicum, Niccolum metallicum, Niccolum sulphuricum, Nicotinamidum, Nicotinum, Nitri spiritus dulcis, Nitricum acidum, Nitrogenum oxygenatum, Nitromuriaticum acidum,* Nosode Kit, Nosode-Select your own, Nuclear Radiation, *Nuphar luteum, Nux moschata, Nux vomica, Nymphaea odorata, Ocimum basilicum, Ocimum canum, Ocimum sanctum, Oenanthe crocata, Oenothera biennis, Olea europaea, Flos, Oleander, Oleum animale, Oleum carvi, Oleum morrhuae, Oleum ricini, Oleum santali, Olibanum, Oniscus, Ononis spinosa, Onopordum, Onosmodium virginianum, Oophorinum, Opuntia vulgaris, Orchitinum, Oreodaphne californica, Origanum majorana, Ornithogalum umbellatum, Ornithogalum umbellatum, Flos, Oroticum acidum, Oscillococcinum, Osmium metallicum, Ostrya, Ova Tosta, Ovi gallinae pellicula, Oxalicum acidum, Oxalis acetosella, Oxydendrum arboreum, Oxytropis lambertii, Paeonia officinalis, Palladium metallicum,* Paloondo, *Pancreas suis, Pancreatinum, Paraffinum, Parathormonum, Parathyroid, Paratyphoidinum B, Pareira brava, Parietaria officinalis, Paris quadrifolia, Paronichia illecebrum, Parotidinum* (Mumps), *Parthenium, Passiflora incarnata, Pastinaca sativa, Paullinia pinnata, Paullinia sorbilis, Pecten, Pediculus capitis, Penicillinum, Penthorum sedoides, Pepsinum, Perhexilinum, Persea americana, Pertussinum* (Whooping Cough), *Petiveria tetrandra, Petroleum, Petroselinum sativum, Phallus impudicus, Phaseolus, Phellandrium aquaticum, Phenacetinum, Phenobarbitalum, Phloridzinum, Phosphoricum acidum, Phosphorus, Physalis alkekenge, Physotigma aenenosum, Phytolacca decandra,* Pichi, *Picricum acidum, Picrotoxinum, Pilocarpinum, Pilocarpinum muriaticum, Pilocarpinum nitricum, Pilocarpus, Pimenta officinalis, Pimpinella saxifraga, Pinus lambertiana, Pinus sylvestris, Pinus sylvestris, Flos, Piper methysticum, Piper nigrum, Piperazinum, Piscidia erythrina, Pituitarum posterium, Pix liquida, Placenta totalis suis,* Plague, *Plantago major, Platanus, Platinum metallicum, Platinum muriaticum, Plectranthus fruticosus, Plumbago littoralis, Plumbum aceticum, Plumbum carbonicum, Plumbum chromicum, Plumbum iodatum, Plumbum metallicum, Pneumococcinum, Podophyllinum, Podophyllum peltatum,* Polio, *Polygonum punctatum, Polygonum sagittatum, Polyporus officinalis, Polyporus pinicola, Populus candicans, Populus tremula, Flos, Populus tremuloides, Potentilla anserina, Pothos foetidus, Primula obconica, Primula veris, Primula vulgaris, Proteus bulgaris, Proteus vulgaris, Prunus ceras-* ifera, Flos, Prunus padus, Prunus spinosa, Prunus virginiana, Psorinum, Ptelea trifoliata, Pulex irritans, Pulsatilla niger, Pulsatilla nuttalliana, Pyrethrum parthenium, Pyridoxinum hydrochloricum, Pyrogenium-sepsis, Pyrus americana, Quassia amara, Quebracho, Quercus glandium spiritus, Quercus robur, Quercus robur, Flos, Quillaja saponaria, Radium bromatum, Ranunculus acris, Ranunculus bulbosus, Ranunculus ficaria, Ranunculus glacialis, Ranunculus repens, Ranunculus sceleratus, Raphanus sativus, Ratanhia, Rauwolfia serpentina, Reserpinum, Resina laricis, Resorcinum, Rhamnus californica, Rhamnus cathartica, Rhamnus frangula, Rhamnus purshiana, Rheum officinale, Rhodium metallicum, Rhododendron chrysanthum, Rhus aromatica, Rhus diversiloba, Rhus glabra, Rhus toxicodendron, Rhus venenata, Riboflavinum, Ricinus communis, RNA, Robinia pseudoacacia, Rock Water, Rosa canina, Rosa canina, Flos, Rosa damascena, Rosmarinus officinalis, Rubella (German Measles), Rubeola (Measles), Rubia tinctorum, Rumex acetosa, Rumex crispus, Rumex obtusifolius, Russula foetens, Ruta graveolens, Sabidilla, Sabal serrulata, Sabina, Saccharinum, Saccharum lactis, Saccharum officinale, Salicinum, Salicylicum acidum, Salix alba, Salix nigra, Salix purpurea, Salix vitellina, Flos, Salmonella, Salol, Salvia officinalis, Samarskite, Sambucus canadensis, Sambucus nigra, Sanguinaria canadensis, Sanguinarinum nitricum, Sanicula, Santoninum, Saponaria officinalis, Saponinum, Sarcode-Select your own organ remedy, Sarcolacticum acidum, Sarracenia purpurea, Sarsaparilla, Sassafras officinale, Scammonium, Scarlatinum, Secale-Ergot schinus molle, Scilla maritima, Scleranthus annuus, Flos, Scolopendra, Scolopendrium vulgare, Scopolaminum hydrobromidum, Scrophularia nodosa, Scutellaria lateriflora, Secale cornutum, Secale-Ergot, Sedum acre, Selenium metallicum, Sempervivum tectorum, Senecio aureus, Senecio jacobaea, Senega officinalis, Senna, Sepia, Serum anguillae, Serum anticolibacillaire, Serum de yersin, Serum equi, Shigella, Silica marina, Silicea, Silphium laciniatum, Sinapis alba, Sinapis arvensis, Flos, Sinapis nigra, Sinusitisinum, Sium latifolium, Skatolum, Skookum chuck, Slag, Solaninum, Solanum arrebenta, Solanum carolinense, Solanum mammosum, Solanum nigrum, Solanum oleraceum, Solanum tuberosum, Solidago virgaurea, Sparteinum sulphuricum, Spigelia anthelmia, Spigelia marilandica, Spilanthes oleracea, Spinacia, Spiraea ulmaria, Spiranthes autumnalis, Spongia encephalitis, Spongia tosta, Stachys betonica, Stannum iodatum, Stannum metallicum, Staphyloccoccus aureus, Staphylococcinum, Staphylotoxinum, Staphysagria, Stellaria media, Sterculia acuminata, Stibium metallicum, Sticta pulmonaria, Stigmata maidis, Stillingia sylvatica, Stramonium, Streptococcinum, Strontium bromatum, Strontium carbonicum, Strontium nitricum, Strophanthus hispidus, Strophanthus sarmentosus, Strychninum, Strychinum arsenicicum, Strychinum nitricum, Strychninum phosphoricum, Strychninum sulphuricum, Succinicum acidum, Succinum, Sulphanilamidum, Sulphonalum, Sulphur, Sulphur hydrogenisatum, Sulphur iodatum, Sulphuricum acidum, Sulphurosum acidum, Sumbul, Symphoricarpus racemosus, Symphytum officinale, Syphilinum (Luesinum), Syzygium jambolanum, Tabacum, Tamus communis, Tanacetum vulgare, Tanghinia venenifera, Tannicum acidum, Taraxacum officinale, Taraxacum officinale, Radix, Tarentula cubensis, Tarentula hispana, Tartaricum acidum, Taxus baccata, Tellurium metallicum, Teplitz, Terebinthina, Tetanotoxinum, Tetradymite, Teucrium marum, Teucrium scorodonia, Thallium metallicum, Thaspium aureum, Thea sinensis, Theobrominum, Theridion, Thiaminum hydrochloricum, Thioproperazinum, Thiosinaminum, Thlaspi bursa-Pastoris, Thuj a lobbi, Thuj a occidentalis, Thymolum, Thymus serpyllum, Thyroidinum, Tilia europaea, Titanium metallicum, Tongo, Tormentilla, Torula cerevisiae, Toxicophis pugnax, Tradescantia diuretica, Tribulus terrestris, Trifolium pratense, Trifolium repens, Trillium pendulum, Trimethylaminum, Triosteum perfoliatum, Triticum repens, Tropaeolum majus, Tuberculinum, Tuberculinum residuum, Tussilago farfara, Tussilago fragrans, Tussilago petasites, Typhoidinum, Ulex europaeus, Flos, Ulmus fulva, Ulmus procera, Flos, Upas tieute, Uranium nitricum, Urea, Uricum acidum, Urtica crenulata, Urtica dioica, Urtica urens, Usnea barbata, Ustilago maidis, Uva-Ursi herb, Uva-Ursi, V.A.B.-BCG, Vaccinium myrtillus, Vaccinotoxinum, Valeriana officinalis, Vanadium metallicum, Varicella enus mercenaria (Chicken Pox), Variolinum (Smallpox), Veratrinum, Veratrum album, Veratrum nigrum, Veratrum viride, Verbascum thapsus, Verbena hastata, Verbena officinalis, Verbena officinalis, Flos, Veronica beccabunga, Veronica officinalis, Vesicaria, Vespa crabro, Viburnum opulus, Viburnum prunifolium, Vinca minor, Viloa odorata, Viola tricolor, Vipera berus, Viscum album, Vitamin B12, Vitamin K, Vitis vinifera, Flos, Wiesbaden, Wyethia helenioides, X-Ray, Xanthoxylum fraxineum, Xerophyllum asphodeloides, Yohimbinum, Yucca filamentosa, Zincum aceticum, Zincum bromatum, Zincum carbonicum, Zincum cyanatum, Zincum gluconicum, Zincum iodatum, Zincum metallicum, Zincum muriaticum, Zincum oxydatum, Zincum phosphoratum, Zincum picricum, Zincum sulphuricum, Zincum valerianicum, Zingiber officinale, and combinations thereof.

Flower essences can also be included in cannabinoid compositions prepared according to the invention. Examples of suitable flower essences include, but are not limited to, Acacia, Actaea, Agrimony, Alpine Lily, Angel's Trumpet, Aloe Vera, Angelica, Basil, Apricot, Arnica Beech, Aspen, Avocado, Beech, Bee Balm, Black Cohosh, Baby Blue Eyes, Black-Eyed Susan, Blackberry, Bloodroot, Calendula, Bleeding Heart, California Fuchsia, California Pitcher Plant, Borage, Buttercup, California Wild Rose, California Poppy, CallaLily, Cerato, Canyon Dudleya, Chamomile, Cayenne, Cedar, Chaparral, Centaury, Centaurium erythraea or Centaurium umbellatum, Cerato, Cherry Plum, Chestnut Bud, Corn, Dandelion, Chicory, Cinquefoil, Coffee, Coreopsis, Crab Apple, Chrysanthemum, Clematis, Desert Dandelion, Deerbrush, Cosmos, Dill, Elm, Evening Primrose, Dogwood, Easter Lily, Eucalyptus, Fairy Lantern, Echinacea, Fawn Lily, Fig, Filaree, Gentian, Goldenrod, Forget-Me-Not, Golden Ear Drops, Golden Yarrow, Fuchsia, Garlic, Gorse, Honeysuckle, Heather, Hornbeam, Hibiscus, Hound's Tongue, Holly, Impatiens, Indian Paintbrush, Larch, Lily, Indian Pink, Larkspur, Iris, Iris douglasiana/Iris versicolor, Lady's Slipper, Cypripedium parviflorum/Cypripedium reginae, Lotus, Lavender, Love-Lies-Bleeding, Mariposa Lily, Madia, Magnolia, Milkweed, Mallow, Mimulus, Manzanita, Morning Glory, Motherwort, Mountain Pennyroyal, Mustard, Mountain Pride, Nasturtium, Mugwort, Nicotiana, Noni, Oak, Olive, Pine, Orange, Oregon Grape, Pansy, Passion Flower, Pear, Petunia, Pink Angel's Trumpet, Pink Monkeyflower, Penstemon, Pink Yarrow Achillea millefolium var. rubra, Peppermint, Poison Oak, Pomegranate, Queen Anne's Lace, Pretty Face, Quince, Purple Monkeyflower, Rabbitbrush, Quaking Grass, Red Chestnut, Red clover, Rescue Remedy, Rock Rose, Sacred Datura, Sagebrush, Scarlet Pimpernel, Rock Water Solarized spring water, Saguaro, Rosemary, Rose, Saint John's Wort, Scarlet Monkeyflower, Shasta Daisy, Scleranthus, Shooting Star, Scotch Broom, Snapdragon, Squash, Self-Heal, Star of Bethlehem, Star Thistle, Sweet Chestnut, Star Tulip, Strawberry, Sun Cup, Sweet Pea, Sticky Monkeyflower, Tansy, Sunflower, Thyme, Tiger Lily, *Trillium*, Violet, Walnut, Trumpet Vine, Vervain, Water Lily, Water Violet, Vine, White Chestnut, Wild Oat, Wild Rose, Yellow Star Tulip, Willow, Yerba Santa, Yarrow, *Yucca, Zinnia*, and combinations thereof.

C. Mouthfeel Experience Enhancers

Formulations of the present invention are adapted to provide or create a desired mouthfeel experience. For example, the formulation can include one or more chemesthetic agents as a mouthfeel experience enhancer. Chemesthetic agents are chemical compounds known to activate receptors involved with pain, touch and thermal perception, such as warming, cooling, stinging, pricking, burning and buzzing. The mouthfeel experience enhancers of the present disclosure are included in the oral formulation to provide or induce an oral sensation such as pungency (warming), freshness, tingling, sharpness, and cooling. For example, in some embodiments the oral formulation (e.g., tablet/lozenge) is formulated to contain pressurized gas bubbles that will release (pop) upon dissolution in the mouth.

The mouthfeel experience enhancer can be a compound that provides a cooling sensation. Xylitol, erythritol, dextrose, sorbitol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Haarman & Reimer, FEMA 3748, tradename FRESCOLAT® type ML), WS-30, WS-14, *Eucalyptus* extract (p-Menthane-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; and Menthol methyl ether, and menthyl pyrrolidone carboxylate among others, are useful cooling agents. In some cases, the cooling agent is erythritol, xylitol, menthol, peppermint oil, mint oil, or a combination thereof.

The mouthfeel experience enhancer can be a compound that provides warmth (warming agents) or a sensory signal of warming in the oral cavity. Useful warming agents include compounds having at least one allyl vinyl component, which may bind to oral receptors. Examples of suitable warming agents include, but are not limited to: vanillyl alcohol n-butylether; vanillyl alcohol n-propylether; vanillyl alcohol isopropylether; vanillyl alcohol isobutylether; vanillyl alcohol n-aminoether; vanillyl alcohol isoamylether; vanillyl alcohol n-hexylether; vanillyl alcohol methylether; vanillyl alcohol ethylether; gingerol; shogaol; paradol; zingerone; capsaicin; dihydrocapsaicin; nordihydrocapsaicin; homocapsaicin; homodihydrocapsaicin; ethanol; isopropyl alcohol; iso-amylalcohol; benzyl alcohol; glycerine; chloroform; eugenol; cinnamon oil; cinnamic aldehyde; phosphate derivatives thereof; and combinations thereof.

The mouthfeel experience enhancer can be a compound that provides a tingling sensation. Tingling agents may be perceived as a tingling, stinging or numbing sensation by the user. Tingling agents include, but are not limited to: Jambu Oleoresin or para cress (*Spilanthes* sp.), in which the active ingredient is Spilanthol; Japanese pepper extract (*Zanthoxylum peperitum*) including Saanshool-I, Saanshool-II and Sanshoamide, or Sichuan pepper including hydroxy-alpha sanshool; black pepper extract (*piper nigrum*), including chavicine and piperine; *Echinacea* extract; Northern Prickly Ash extract; and red pepper oleoresin.

In some cases, the tingling is produced by effervescence. Thus, the mouthfeel experience enhancer can be a compound or combination of compounds that produce effervescence (e.g., an alkaline material and an acidic material). Either or both the compounds can be encapsulated or otherwise separated in the oral formulation, to be activated or interact in the oral cavity upon release. In some embodiments, an alkaline material may include alkali metal carbonates, alkali metal bicarbonates, alkaline earth metal carbonates, alkaline earth metal bicarbonates and mixtures thereof. In some embodiments, an acidic material may include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof.

Other mouthfeel experience enhancers for use in the oral formulations include at least one compound that creates or tends to create a puckering sensation (sharpness), or that induces salivation, such as an acidulant or sialogogue. Exemplary acidulants include gluconolactone, citric acid, malic acid, acetic acid, phosphoric acid, tartaric acid, lactic acid, fumaric acid, succinic acid adipic acid, ascorbic acid, butyric acid, formic acid, fumaric acid, glyconic acid, phosphoric acid, oxalic acid, succinic acid, and the like. The salivation inducing agent can include tasteless compounds that increase the flow rate of saliva by more than 10%, e.g., at least about 12% or at least about 16% or at least about 18%. Examples of suitable salivation inducing agents include, but are not limited to, those tasteless muscarinic acetylcholine receptor agonists such as pilocarpine and the compound that is commercially available from IFF under the tradename, "SN12011;" sigma binders such as arylalkylamines wherein the alkyl group has from about 1 to about 8 carbons, i.e., e.g., N,N-disubstituted phenylalkylamines wherein the alkyl has from about 1 to about 8 carbons and N,N disubstituted-2-phenylcyclopropylamines; spirooxathiolane-quinnuclidine; *Heliopsis* longpipes root; cholinesterase inhibitors; and mixtures thereof.

In some embodiments, the formulations include a mouthfeel experience enhancer that stimulates a tingling sensation, such as hydroxy-alpha-sanshool as found in Szechuan peppercorns, Szechuan button and the like, or that stimulates a warming sensation, such as capsaicin as found in peppers from the *Capsicum annuum* species and their relatives, as well as isolates therefrom, and isolated capsaicin.

D. Oral Formulations

Oral formulations of the present disclosure can have any form suitable for delivering the active agent within the oral cavity (e.g., buccally, sublingually, or transmucosally), or within the gastrointestinal tract. For example, orally dissolvable or dispersible forms such as suckable and chewable dosage forms, orally disintegrating forms, lozenges; lollipops; mucoadhesive films, oral solutions, buccal patches and sprays, sublingual droplets, microencapsulates, and tablets are known in the art for intraoral or peroral administration.

Oral formulations of the present disclosure include compressed tablets and compressed tablet lozenges (i.e., a troche or lozenge made by compression of a granulate that is prepared in a manner similar to that used for any compressed tablet). The compressed tablet can be a chewable tablet. A compressed tablet lozenge differs from conventional tablets in terms of organolepticity, non-disintegrating characteristics and slower dissolution profiles. In some cases, the compressed tablet lozenge is made using heavy compression equipment to produce a dosage form that is harder than a tablet, to allow the dosage form to dissolve slowly in mouth. The granulate can include at least one excipient such as dextrose, sucrose, or other sugars, sugar free vehicles such as mannitol, sorbitol, polyethylene glycol (PEG) 6000 and 8000, fillers including dicalcium phosphate, calcium sulphate, calcium carbonate, lactose and microcrystalline cellulose, binders such as *acacia*, corn syrup, sugar syrup, gelatin, polyvinyl-pyrrolidone, tragacanth and methylcellulose, lubricants such as magnesium stearate, calcium stearate, stearic acid and PEG. In some cases, the granulate includes at least one color or flavorant.

In some cases, the oral formulation is a molded tablet, hard candy lozenge (e.g., a pastille), or soft lozenge (i.e., a lozenge intended to be chewed or for slow drug release in mouth). Molded tablets are generally prepared by mixing the active drug with lactose, dextrose, sucrose, mannitol, or other appropriate diluent that can serve as the water-soluble base. A soft lozenge can include PEG 1000 or 1450, chocolate or sugar-*acacia* base. In some cases, a soft lozenge can be formed from a soft candy composition comprising *acacia* and silica gel. The hard candy lozenge can be formulated to undergo a slow and uniform dissolution or erosion over 5-10 minutes, without disintegration.

The total lozenge or tablet mass may range from 400 mg to 2000 mg, depending on particular consumer preferences and desired performance attributes such as lozenge residence time (dissolution) in the mouth.

Tablets and lozenges of the present disclosure can be formulated to provide controlled release or pulsatile release, as a multi-part composition. The multi-part composition may be physically constructed as a layered tablet or lozenge, a tablet, coated tablet, or a formed lozenge with an outer layer having a rapid acting component and an inner core with delayed release of any active therein, film-coated granules of an active embedded within an excipient matrix. For example, a lozenge can be a multilayer lozenge, a coated lozenge or a combination of layers and coatings. A compressed tablet lozenge can include at least two layers, a core and an outer layer covering the core. The core can be spherical, and the coating can be concentrically arranged over the surface of the core. The core can be compression coated, dip coated, spray-coated, or fluidized bed-coated. In some embodiments the lozenges are made up of multiple layers arranged on top of each other. In some embodiments the formulations are lozenges having a combination of candy-style and compressed tablet-style layers.

In some embodiments the oral dosage form (e.g., tablet or lozenge) is coated. The coating can be a sugar coating or polymeric film coating. The coating can include at least one mouthfeel experience enhancer, cannabinoid, and mixtures thereof. In some cases, the coating can include a coloring agent (e.g., a pigment, dye, lake, or opacifier). Different colors can be used to differentiate specific formulations. For example, a specific color can be associated with a single delivery profile, cannabinoid, mouthfeel experience, or the like. In some embodiments, the formulation is coated with a single layer coating (e.g., controlled release film coating or a seal coating). In other embodiments, the formulation includes multiple layers of coating.

In a specific embodiment, the oral formulation is a candy style lozenge comprising a cannabinoid and a mouthfeel experience enhancer. The candy style lozenge can be a pastille The lozenge can be made from a sugar base, or a non-nutritive ingredient, optionally a sugar alcohol. In some embodiments the lozenge comprises at least two concentric layers or at least two stacked layers.

Various kinetic release modes can be used in different embodiments. For example, an oral formulation of the present disclosure can be adapted for zero order sustained release, quick/slow delivery system, time programmed delivery, and bimodal release by varying the geometry, arrangement, or excipients of a multilayer dosage form. In addition, a multilayer tablet can be designed for to achieve a specific dissolution pattern for providing pulsatile, bimodal, delayed and multi modal delivery of one or more cannabinoids or mouthfeel experience enhancers.

In some embodiments, a tablet or lozenge of the present disclosure exhibits zero order sustained release. The oral formulation can comprise a hydrophilic or hydrophobic polymeric matrix. Release of the active can be controlled by a polymeric film layer one side of the matrix, leaving other sides for exposure to the dissolution medium to sustain the release of the active.

In some embodiments, a tablet or lozenge of the present disclosure exhibits a quick/slow release characterized by initial rapid release followed by extended/prolonged release of the active to achieve an immediate therapeutic effect and to sustain a constant release of the active to maintain the desired effect.

In some embodiments, a tablet or lozenge of the present disclosure provides a time programmed delivery of the active characterized by immediate release of the active followed by time controlled release when the delivery of active is required in a time controlled fashion in the mouth. For example, time controlled release can be achieved by incorporating a core which is coated with a hydrophobic or hydrophilic polymeric barrier layer. The release of active from the core is delayed until after swelling/eroding of hydrophobic or hydrophilic barrier of coating.

In some embodiments, a tablet or lozenge of the present disclosure exhibits a bimodal release profile characterized by an initial rapid release followed by slow release and again a second phase of active drug release i.e., sigmoidal release profile.

Tablets or lozenges of the present disclosure can be multilayer dosage forms comprising two, three, or four layers. A bi-layer tablet can be used for sequential and simultaneous release of two different actives, or the same active formulated for different rates of release. For example, one layer is immediate release and another layer is sustained release which acts as a maintenance dose. A triple layer tablet or lozenge can include at least two active containing layers. For example, the dosage form can include a first layer for immediate release of drug, a second layer for sustained release. The first and second layers can be separated by a middle barrier layer. The multilayer tablet can provide multiple release kinetics profile in single delivery system of one or more actives. An immediate release layer can be formulated as a disintegrating monolithic matrix to achieve an initial peak of cannabinoid, and a sustained release layer can be formulated as an erodible monolithic matrix to deliver the active later to maintain a mouthfeel experience while the dosage form is in the oral cavity.

In some cases, the formulation is an oral solution. The dosage form can be packaged to be delivered as a spray or spritz. In such embodiments the excipients used may include medium chain triglycerides or other suitable diluents known to those having skill in the art.

In an embodiment, the formulation is a mucoadhesive format, such as, a dissolvable film, or a mucoadhesive patch or buccal tablet. Methods of manufacture for such formats are known to those having skill in the art.

In some embodiments the formulations contain a flavorant, including but not limited to a natural flavor, such as, for example those derived from the essential oils, oleoresins, essences, extractives, powders, distillates, or any product which contains the flavoring constituents derived from a spice, fruit, or fruit juice, vegetable juice with the significant function of flavoring any of the embodiments/formulations disclosed herein. In some embodiments, flavoring or agents adapted to create the sensation of "umami" such as monosodium glutamate, soy sauce, or the like are included.

The dosage form may contain other excipients typically used in pharmaceutical formulation including, but are not limited to fillers, including water soluble compressible carbohydrates such as sucrose, mannitol, sorbitol, maltitol, xylitol, erythritol, lactose, isomalt, lactitiol, dextrose, polydextrose, dextrose monohydrate, fructose, maltose and mixtures thereof; conventional dry binders including cellulose, cellulosic derivatives, polyvinyl pyrrolidone, starch, modified starch, maltodextrin, and mixtures thereof, and in particular microcrystalline cellulose, maltodextrin, and starch; sweeteners including aspartame, acesulfame potassium, sucralose and saccharin; disintegrants such as microcrystalline cellulose, starch, sodium starch glycolate, crosslinked polyvinylpyrrolidone, crosslinked carboxymethylcellulose; preservatives, flavors, acidulants, antioxidants, lubricants, glidants, surfactants, and coloring agents. The oral formulation of claim 1, further containing at least one sugar alcohol. In some cases, the dosage form includes a hydrocolloid selected from the group consisting of gelatin, gum *acacia*, carob gum, carrageenan, ghatti gum, guar gum, karaya gum, pectin, tragacanth gum, locust bean gum, xanthan gum and combinations thereof.

The dosage forms of the present invention may be made by any means known in the art. For example, conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art. In embodiments wherein the tablets are formed by the direct compression method, the desired blend of active ingredients, salivation inducing agent, and optional ingredients are blended, then a pre-determined volume of particles is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar.

In some embodiments, preparing the dosage for includes additional processing of the cannabinoid actives to facilitate delivery across buccal membranes. Transfer of medicament through the interstices between or through epithelial cells is primarily governed by the lipid solubility of the medicament. In the case of a water-insoluble drug, absorption from the sublingual area is limited. There are therefore physical and biological limitations on the therapeutic usefulness of lipophilic medicaments, such as cannabinoids, given by mouth and swallowed. In some embodiments of the formulations of the present disclosure, the cannabinoids and/or combinations thereof are processed to improve bioavailability/solubility/hydrophilicity using any methods known to those having skill in the art, and thereby facilitate oral delivery. For example, compositions including but not limited to emulsions, microemulsions, and nanoemulsions can provide improved bioavailability and solubility of a cannabinoid. Encapsulation, complexation with solubility enhancers such as, for example, a cyclodextrin (e.g., beta cyclodextrins, SBE-beta-cyclodextrins and the like); and complexation with sugar alcohols such as, for example erythritol, isomalt and the like can improve hydrophilicity and solubility of the cannabinoid. In some embodiments the formulations of the present invention are made by combining a water-soluble cannabinoid powder referred to herein as "a sugar alcohol (or sugar) intermediate" with the other components of the formulation (e.g., the tableting blend) to provide the at least one cannabinoid to the final formulation. The sugar alcohol intermediate may be prepared by the procedure set forth in the Examples below.

Formulations of the present disclosure can be used to address a variety of diseases and/or medical conditions. In some embodiments, the diseases include, but are not limited to, Acquired Hypothyroidism, Acute Gastritis, Acute Pain, Adrenal Disease, Agoraphobia, AIDS Related Illness, Alcohol Abuse, Alcoholism, Alopecia Areata, Alzheimer's Disease, Amphetamine Dependency, Amyloidosis, Amyotrophic Lateral Sclerosis (ALS), Angina Pectoris, Ankylosis, Anorexia, Anorexia Nervosa, Anxiety Disorders, any Chronic Medical Symptom that Limits Major Life Activities, Arteriosclerotic Heart Disease, Arthritis, Arthritis (Rheumatoid), Arthropathy, Gout, Asthma, Attention Deficit Hyperactivity Disorder (ADD/ADHD), Autism/Asperger's, Autoimmune Disease, Back Pain, Back Sprain, Bell's Palsy, Bipolar Disorder, Brain Tumor, Breakthrough Pain, Malignant, Bruxism, Bulimia, Cachexia, Cancer, Carpal Tunnel Syndrome, Cerebral Palsy, Cervical Disk Disease, Cervicobrachial Syndrome, Chemotherapy Chronic Fatigue Syndrome, Chronic Pain, Chronic Renal Failure, Cocaine Dependence, Colitis, Collagen-Induced Arthritis, Colorectal Cancer, Conjunctivitis, Constipation, Crohn's Disease, Cystic Fibrosis, Damage to Spinal Cord Nervous Tissue, Darier's Disease, Degenerative Arthritis, Degenerative Arthropathy, Delirium Tremens, Dermatomyositis, Diabetes, Diabetic Neuropathy, Diabetic Peripheral Vascular Disease, Diarrhea, Digestive Diseases, Diverticulitis, Dysthymic Disorder, Dystonia, Eczema, Emphysema, Emphysema, Endometriosis, Epidermolysis Bullosa, Epididymitis, Epilepsy, Felty's Syndrome, Fibromyalgia, Friedreich's Ataxia, Gastritis, Genital Herpes, Gliomas, Glaucoma, Glioblastoma Multiforme, Graves Disease, Cluster Headaches, Migraine Headaches, Tension Headaches, Hemophilia A, Henoch-Schonlein Purpura, Hepatitis C, Hereditary Spinal Ataxia, HIV/AIDS, HIV-Associated Sensory Neuropathy, Hospice Patients, Huntington's Disease, Hypertension, Hypertension, Hyperventilation, Hypoglycemia, Impotence, Inflammatory autoimmune-mediated arthritis, Inflammatory Bowel Disease (IBD), Insomnia, Intermittent Explosive Disorder (IED), Intractable Pain, Intractable Vomiting, Lack of Appetite, Lipomatosis, Lou Gehrig's Disease, Lyme Disease, Lymphoma, Major Depression, Malignant Melanoma, Mania, Melorheostosis, Meniere's Disease, Methicillin-Resistant *Staphylococcus aureus* (MRSA) Infections, Motion Sickness, Mucopolysaccharidosis (VIPS), Multiple Sclerosis (MS), Muscle Spasms, Muscular Dystrophy, Myeloid Leukemia, Movement Disorders, Nail-Patella Syndrome, Neurogenic Pain, Nightmares, Obesity, Obsessive Compulsive Disorder, Opiate Dependence, Osteoarthritis, Panic Disorder, Parkinson's Disease, Peripheral Neuropathy, Peritoneal Pain, Persistent Insomnia, *Porphyria*, Post Polio Syndrome (PPS), Post-traumatic arthritis, Post-Traumatic Stress Disorder (PTSD), Premenstrual Syndrome (PMS), Prostatitis, Pruritus, Psoriasis, Pulmonary Fibrosis, Quadriplegia, Radiation Therapy, Raynaud's Disease, Reiter's Syndrome, Restless Legs Syndrome (RLS), Rheumatoid Arthritis, Rosacea, Schizoaffective Disorder, Schizophrenia, Scoliosis, Sedative Dependence, Seizures, Senile Dementia, Severe Nausea, Sexual Disorders, Skin Tumors, Shingles (Herpes Zoster), Sickle-Cell Disease, Sinusitis, Skeletal Muscular Spasticity, Sleep Apnea, Sleep Disorders, Spasticity, Spinal Stenosis, Sturge-Weber Syndrome (SWS), Stuttering, Tardive Dyskinesia (TD), Temporomandibular Joint Disorder (TMJ), Tenosynovitis, Terminal Illness, Thyroiditis, Tic Douloureux, Tietze's Syndrome, Tinnitus, Tobacco Dependence, Tourette's Syndrome, Trichotillomania, Unintentional Weight Loss, Viral Hepatitis, Vomiting, Wasting Syndrome, Whiplash, Wittmaack-Ekbom's Syndrome, Writers' Cramp, and combinations thereof.

The following examples illustrate an embodiment of the present disclosure and should not be construed as to narrow its scope.

EXAMPLES

Sugar Alcohol (or Sugar) Intermediate i. Prepare a Concentrated Oil (CO) Formulate:

Calculate quantities of the one or more cannabinoid containing oils to add in order to achieve a desired potency/concentration and/or cannabinoid ratio. Heat oil, or oils, to workable fluidity (e.g., 50-60° C.).

For cannabinoid mixtures, add each cannabinoid containing oil into a clean appropriately sized vessel until reaching quantity setpoints determined by formulation calculations (±1 g desired mass). Seal vessel and heat, mixing well until homogeneous. Measure density of CO Formulate by pulling 1 mL in a pipette, taring the scale, and emptying pipette back into vessel as (average of pulls in triplicate). Confirm the concentration/ratio by quantitating the cannabinoids of interest in the CO Formulate via HPLC or other suitable analytical technique. Adjust formulation as needed to achieve target cannabinoids amount and/or ratio and verify adjusted formulation by HPLC or other suitable analytical technique.

ii. Prepare a Solvent Formulate:

Calculate quantities of CO Formulate and solvent (ethanol) needed. Heat CO Formulate to workable fluidity (50-60° C.). Slowly adding each component in an appropriately sized vessel until reaching setpoints determined by formulation calculations (±1 g desired mass). Typical ratio is 1:1, i.e., 1 part CO Formulate to 1 part 200 proof ethanol, or similar solvent or mixture thereof. The Ethanol Formulated is sonicated in a bath sonicator.

In some cases, the Ethanol Formulate is homogenized with a probe sonicator. A taller, thinner vessel is preferred over a shorter, wider one for sonication. Sanitize probe by wiping with 200 proof ethanol before sonicating. Run sonicator per manufacturer's recommendations according to substrate volume, viscosity, composition, etc. Place vessel containing Ethanol Formulate in ice bath to keep solution cool during sonication. (e.g., dry ice and ethanol or water when available, or mixture of ice, water, and rock salt). Set temperature probe and sonicator probe in vessel. The tip of the sonicator probe should be about ⅓ from top of Ethanol Formulate. Ensure the sonicator probe never touches any glass or metal.

During the sonication process, the vessel is watched to verify it does not move or touch sonication probe. If temperature exceeds setpoint, the program should automatically pause. When this happens, wait for solution to reach below 30° C. and restart program. When finished, remove vessel from sonicator. Clean sonicator and temperature probes. Dispose of ice bath. The homogenized Ethanol Formulate is filtered (e.g., a 200 nm filter).

iii. Prepare a Sugar Alcohol (or Sugar) Formulate:

Melt sugar or sugar alcohol. It takes about 55 minutes to melt 800 g isomalt in one 9"×13" Pyrex baking dish. Larger quantities of isomalt can take several hours to melt completely. Using figures from Formulation calculations to provide a specific dose of cannabinoid (e.g., 10 mg/per dosage unit) measure isomalt into each Pyrex baking dish until total amount is achieved. Heat isomalt in oven until it becomes a uniform, clear liquid. Remove from oven immediately to avoid discoloration and off flavors (a burnt flavor).

While isomalt is heating, prepare mixing equipment and additional components (Quillaja extract (exemplary emulsifier) and gum Arabic (exemplary hydrocolloid)). A mixing container (such as a silicone pot or stainless pot) is cleaned and sanitized. When added to the isomalt, the quillaja extract will cause foaming. A suitably sized container will be at least 3 or 4 times the volume of the isomalt. Pre-measure quillaja extract per Formulation calculations in small beaker. Pre-measure gum Arabic in small beaker. When the isomalt is a clear, hot liquid, remove from oven and empty into silicone pot. While stirring, pour quillaja extract and half of the gum Arabic into isomalt. Keep stirring until foaming subsides and mixture is uniform in color.

Per Formulation calculations, add pre-determined amount of Ethanol Formulate. One method is to tare scale with vessel containing Ethanol Formulate. Pour Ethanol Formulate until scale shows the desired quantity has been removed. It is better to over-pour than to under-pour as the concentration can be reduced in the Final Formulation as needed. Ethanol will start evaporating once it hits hot isomalt, thereby removing the ethanol. This step should be done in a fume hood whenever possible. Keep stirring until color is uniform.

While hot, pour the molten mixture of isomalt, quillaja extract, gum Arabic, and *cannabis* oil mixture out onto suitable surface and spread, while hot, as thin of a layer as possible. Allow to cool to room temperature to solidify. The cooling process can be accelerated by cooling on and/or under dry ice.

iv. Prepare the Sugar Alcohol (or Sugar) Intermediate

Once the isomalt formulate is completely cooled (no longer tacky and at room temperature) it can be broken into smaller pieces, aka "shards". The hardness can be tested with a clean utensil—if the isomalt formulate does not allow deformation with a pointed utensil, it is ready to be broken. Cover the isomalt formulate to prevent isomalt shards from flying during the breaking process. Use hammer or hands or other suitable tools to break the solid sheet of isomalt formulate into small pieces.

Add the isomalt formulate shards to a collection vessel. Get a final weight of isomalt formulate added. Add remaining gum Arabic as a lubricant for size reduction. Total gum Arabic content is 1-2% of the mass of the isomalt formulate. Mix as well as possible to ensure the maximum amount of isomalt formulate is coated with gum Arabic powder. Record the amount of gum Arabic added. Mill Isomalt Formulate Shards into a powder of desired particle size using a mill or other appropriate equipment. The bulk powder was subjected to mechanical separation and filtering to provide a powder having a particle size of no greater than 600 microns.

Exemplary Dosage Forms Containing the Sugar Alcohol Intermediate and Mouthfeel Experience Enhancer The resulting water-soluble cannabinoid powder can be combined with a lozenge or tablet base with or without a mouthfeel experience enhancer. In some cases, the formulation base includes excipients using conventional amounts, equipment, and methods for direct compression of a specific dosage of cannabinoid, which can be layered or coated with a formulation comprising a mouthfeel experience enhancer. Alternatively, the soluble cannabinoid powder can be combined with the mouthfeel experience enhancer as active ingredients of a solution or suspension (e.g., an oral spray) with one or more inert ingredients, selected from the group consisting of organic solvents, emulsifiers, flavor modifiers, and antifoam agents, in oil or water.

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

With respect to the above, it is to be understood that the invention is not limited in its application to the details of construction and to the arrangement of the components listed or the steps set forth in the description or illustrated in the drawings. The various apparatus and methods of the disclosed invention are capable of other embodiments, and of being practiced and carried out in various ways that would be readily known to those skilled in the art, given the present disclosure. Further, the terms and phrases used herein are for descriptive purposes and should not be construed as in any way limiting.

As such, those skilled in the art will appreciate that the conception upon which this disclosure is based may be utilized as a basis for designing other inventions with similar properties. It is important therefore that the embodiments, objects, and claims herein, be regarded as including such equivalent construction and methodology insofar as they do not depart from the spirit and scope of the present invention.

What is claimed is:

1. An oral formulation comprising at least one cannabinoid and at least one mouthfeel experience enhancer, wherein the at least one mouthfeel enhancer comprises a tingling agent selected from the group consisting of Japanese pepper extract, Szechuan peppercorn or an extract thereof, sanshool-I, sanshool-II, hydroxy-alpha-sanshool, and sanshoamide, and wherein the oral formulation is a hard candy lozenge formulated to undergo a slow and uniform dissolution or erosion over 5-10 minutes, without disintegration, and wherein the formulation does not include a soft candy composition, wherein the lozenge comprises a core and an outer layer, wherein the core comprises tetrahydrocannabinol and cannabidiol and the outer layer comprises Szechuan peppercorn or an extract thereof.

2. An oral formulation comprising at least one cannabinoid and at least one mouthfeel experience enhancer, wherein the at least one mouthfeel enhancer comprises a tingling agent selected from the group consisting of Japanese pepper extract, Szechuan peppercorn or an extract thereof, sanshool-I, sanshool-II, hydroxy-alpha-sanshool, and sanshoamide, and wherein the oral formulation is a hard candy lozenge formulated to undergo a slow and uniform dissolution or erosion over 5-10 minutes, without disintegration, and wherein the formulation does not include a soft candy composition, wherein the lozenge comprises an intermediate layer disposed between a core and an outer layer, wherein the core comprises a first cannabinoid and Szechuan peppercorn or an extract thereof and a second mouthfeel experience enhancer, the intermediate layer comprises a second cannabinoid and a third mouthfeel experience enhancer, and the outer layer comprises at least a third cannabinoid.

3. The oral formulation of claim 2, wherein the second and the third mouthfeel experience enhancers are independently selected from the group consisting of a warming agent, tingling agent, cooling agent, puckering agent and sialagogue.

4. The oral formulation of claim 2, wherein the first, the second and the third cannabinoids are independently selected from the group consisting of tetrahydrocannabinol, tetrahydrocannabinolic acid, cannabidiol, cannabidiolic acid, cannabigerol, cannabichromene, tetrahydrocannabivarin, and combinations thereof.

* * * * *